United States Patent
Yun et al.

(10) Patent No.: US 9,448,231 B2
(45) Date of Patent: Sep. 20, 2016

(54) APPLICATION OF QUANTUM DOTS FOR NUCLEAR STAINING

(75) Inventors: Chol Steven Yun, Tucson, AZ (US); Brian Daniel Kelly, Tucson, AZ (US); Julia Ashworth-Sharpe, Tucson, AZ (US); Christopher A. Bieniarz, Tucson, AZ (US); Pascal Bamford, Dublin, CA (US); Adrian E. Murillo, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 308 days.

(21) Appl. No.: 13/402,567

(22) Filed: Feb. 22, 2012

(65) Prior Publication Data

US 2012/0219948 A1   Aug. 30, 2012

Related U.S. Application Data

(60) Provisional application No. 61/464,217, filed on Feb. 28, 2011.

(51) Int. Cl.
    *C12Q 1/68* (2006.01)
    *G01N 33/53* (2006.01)
    (Continued)

(52) U.S. Cl.
    CPC ............ *G01N 33/5308* (2013.01); *B82Y 15/00* (2013.01); *C12Q 1/6816* (2013.01); *G01N 33/588* (2013.01)

(58) Field of Classification Search
    CPC .......... G01N 33/53083; C12Q 1/6816; C12Q 2563/155
    USPC ................................ 977/704; 435/6.1, 6.11
    See application file for complete search history.

(56) References Cited

U.S. PATENT DOCUMENTS

| 5,990,479 A | 11/1999 | Weiss et al. |
| 6,468,808 B1 | 10/2002 | Shuming et al. |

(Continued)

FOREIGN PATENT DOCUMENTS

| CA | 2661713 A1 | 3/2008 |
| JP | 2003522962 A | 7/2003 |

(Continued)

OTHER PUBLICATIONS

Stratagene catalog 1988, p. 39.*

(Continued)

*Primary Examiner* — Jezia Riley
(74) *Attorney, Agent, or Firm* — Ventana Medical Systems, Inc.

(57) ABSTRACT

Embodiments of a system, method, and kit for visualizing a nucleus are disclosed. A tissue sample is pretreated with a protease to permeabilize the nucleus, and then incubated with a nanoparticle/DNA-binding moiety conjugate. The DNA-binding moiety includes at least one DNA-binding molecule. The conjugate binds to DNA within the nucleus, and the nanoparticle is visualized, thereby visualizing the nucleus. Computer and image analysis techniques are used to evaluate nuclear features such as chromosomal distribution, ploidy, shape, size, texture features, and/or contextual features. The method may be used in combination with other multiplexed tests on the tissue sample, including fluorescence in situ hybridization. Kits for performing the method include a protease enzyme composition, a nanoparticle/DNA-binding moiety conjugate, and a reaction buffer.

16 Claims, 13 Drawing Sheets

(7 of 13 Drawing Sheet(s) Filed in Color)

(51) Int. Cl.
    B82Y 15/00      (2011.01)
    G01N 33/58      (2006.01)

(56) References Cited

U.S. PATENT DOCUMENTS

| | | |
|---|---|---|
| 6,649,138 B2 | 11/2003 | Adams et al. |
| 6,682,596 B2 | 1/2004 | Zehnder et al. |
| 6,815,064 B2 | 11/2004 | Treadway et al. |
| 6,921,496 B2 | 7/2005 | Anderson et al. |
| 7,498,177 B2 | 3/2009 | De La Fuente et al. |
| 7,574,304 B2 | 8/2009 | Jackway et al. |
| 2002/0072069 A1 | 6/2002 | Ford et al. |
| 2002/0127224 A1 | 9/2002 | Chen |
| 2003/0147966 A1* | 8/2003 | Franzen et al. ............... 424/491 |
| 2005/0012182 A1 | 1/2005 | Jang et al. |
| 2006/0246524 A1 | 11/2006 | Bauer et al. |
| 2007/0117153 A1 | 5/2007 | Bieniarz et al. |
| 2008/0118941 A1 | 5/2008 | Chen et al. |
| 2009/0053725 A1 | 2/2009 | Holwitt et al. |
| 2010/0133487 A1 | 6/2010 | Kawamoto et al. |
| 2010/0298536 A1 | 11/2010 | Park et al. |

FOREIGN PATENT DOCUMENTS

| | | |
|---|---|---|
| JP | 2004065040 A | 3/2004 |
| JP | 2005-069778 | 3/2005 |
| WO | 0161040 A1 | 8/2001 |
| WO | WO 2005/001889 | 1/2005 |
| WO | 2006116742 A2 | 11/2006 |
| WO | WO 2008/098248 | 8/2008 |
| WO | 2011/011782 A1 | 1/2011 |

OTHER PUBLICATIONS

Bentolila et al., "Single-step multicolor fluorescence in situ hybridization using semiconductor quantum dot-DNA conjugates," *Cell Biochemistry and Biophysics* 45(1):59-70, 2006.

Biju et al., "Delivering quantum dots to cells: bioconjugated quantum dots for targeted and nonspecific extracellular and intracellular imaging," *Chemical Society Reviews* 39:3031-3056, 2010.

Chen et al., "Fluorescent CdSe/ZnS nanocrystal-peptide conjugates for long-term nontoxic imaging and nuclear targeting in living cells," *Lawrence Berkley National Laboratory*, Mar. 29, 2005 (escholarship.org/uc/item/5wj4q3m).

Delehanty et al., "Delivering quantum dots into cells: strategies, progress and remaining issues," *Anal Bioanal Chem* 393:1091-1105, 2009.

Dubertret, "Quantum dots—DNA detectives," *Nature Materials* 4(11):797-798, 2005.

Ebenstein et al., "Lighting Up Individual DNA Binding Proteins with Quantum Dots," *Nano Letters* 9(4):1598-1603, 2009.

International Search Report dated Aug. 6, 2012, from International Application No. PCT/EP2012/053255.

Ishihama et al., "Single molecule tracking of quantum dot-labeled mRNAs in a cell nucleus," *Biochemical and Biophysical Research Communication* 381:33-38, 2009.

Mehrabi et al., "Intercalating Gold Nanoparticles as Universal Labels for DNA Detection," *Small* 3(9):1491-1495, 2007.

Pindur et al., "Advances in DNA-Ligands with Groove Binding, Intercalating and/or Alkylating Activity: Chemistry, DNA-Binding and Biology," *Current Medicinal Chemistry* 12:2805-2847, 2005.

Puchkov et al., "Locating of Nucleic Acid Intercalators in Yeast Cells by Image Analysis Combined Fluorescence Microscopy," *Journal of Fluorescence* 21:1009-1013, 2011.

Rodenacker et al., "a feature set for cytometry on digitized microscopic images," *Analytical Cellular Pathology* 25:1-36, 2003.

Rosenthal et al., "Biocompatible Quantum Dots for Biological Applications," *Chemistry & Biology* 18:10-24, 2011.

Walther et al., "Quantum Dot—Carrier Peptide Conjugates Suitable for Imaging and Delivery Applications," *Bioconjugate Chem.* 19:2346-2356, 2008.

Wang et al., "In vitro and in vivo imaging with quantum dots," *Anal Bioanal Chem* 397:1397-1415, 2010.

Wang et al., "Quantum dots, lighting up the research and development of nanomedicine," Nanomedicine: Nanotechnology, Biology, and Medicine 7:385-402, 2011.

Written Opinion dated Aug. 6, 2012, from International Application No. PCT/EP2012/053255.

Xu et al., "Cell Nucleus Penetration by Quantum Dots Induced by Nuclear Staining Organic Fluorophore and UV-Irradiation," *Advanced Materials* 20:3468-3473, 2008.

Zhang et al., "Fluorescent quantum dot-labeled aptamer bioprobes specifically targeting mouse liver cancer cells," *Talanta* 81:505-509, 2010.

Zhao et al., "NAC-Capped Quantum Dot as Nuclear Staining Agent for Living Cells via an In Vitro Steering Strategy," *J. Phys. Chem.* 114:6216-6221, 2010.

Ting, B.P., et al., "A DNA biosensor based on the detection of doxorubicin-conjugated Ag nanoparticle labels using solid-state voltammetry," Biosensors an Bioelectronics 25 (2009),pp. 282-287.

Wang, G., et al., "DNA Binding of an Ethidium Intercalator Attached to a Monolayer-Protected Gold Culster," Ana. Chem., (2002), 74, pp. 4320-4327.

Algar et al., Beyond labels: A review of the application of quantum dots as integrated components of assays, bioprobes, and biosensors utilizing optical transduction, Analytica Chimica Acta, 673, 2010, pp. 1-26.

Furuta et al, In Situ Hybridization with Non-Isotopic Probes for Detection of Viral Genomes, Journal of Chemical and Experimental Medicine, May 18, 1991, pp. 100-403, vol. 157, No. 7.

Notice of Reasons for Rejection mailed Dec. 1, 2015 for corresponding JP Application No. 2013-555840.

Takano, In Situ PCR—A method of detecting one copy of DNA or mRNA while preserving localization, Journal of Clinical and Experimental Medicine (Igaku no Ayumi), Oct. 18, 1997, pp. 233-237, vol. 183, No. 3.

Canadian Office Action mailed Apr. 8, 2016 in corresponding Canadian Patent Application No. 2824355.

* cited by examiner

APPLICATION OF QUANTUM DOTS FOR NUCLEAR STAINING

CROSS REFERENCE TO RELATED APPLICATIONS

This application claims the benefit of the earlier filing date of U.S. Provisional Application No. 61/464,217, filed Feb. 28, 2011, which is incorporated herein in its entirety.

FIELD

The present invention relates generally to a system and method for nuclear staining in tissue samples. Quantitative nuclear measurements can be obtained from pathology samples under fluorescence microscopy examination. In certain embodiments, the present invention provides a method for simultaneously measuring nuclear morphology and texture with other multiplexed tests on the same slide.

BACKGROUND

The measurement of nuclear characteristics by automated image analysis is a powerful approach in the detection, diagnosis and prognosis of various disease states. These characteristics have traditionally included morphology, ploidy, texture and contextual features. One of the most successful embodiments of this technology has been applied to mass cervical cancer screening in the form of commercial imaging systems from Hologic™ (the ThinPrep® Imaging System) and Becton, Dickinson and Company (Focal-Point™). Other commercial systems include OralAdvance™ and LungSign™ from Perceptronix Medical Inc. Laboratories for the early detection of oral and lung cancer respectively.

Nuclear morphology generally pertains to shape and size measurements; such as those describing perimeter roundness. Ploidy is generally applied via a stoichiometric staining protocol (e.g. Thionin-Feulgen) to determine abnormal chromosome counts, termed aneuploidy, and involves measuring integrated optical density across the nuclear area. Texture analysis methods are generally considered as either statistical or structural. Both approaches produce descriptive measures of the spatial and intensity variation of a nucleus' internal structure, or chromatin pattern. Finally, contextual features measure the spatial distribution of inter-nuclear arrangements within a tissue structure.

All of these methods have been applied individually and in combination to successfully discriminate between normal and abnormal pathology in various tissue types. While the focus of this work has generally been applied to bright-field imaging, some research has also been conducted on the evaluation of such approaches to fluorescence microscopy.

However, traditional fluorophores suffer from several problems that reduce their utility in the application of such techniques to this modality. Photobleaching is a key issue that degrades the signal of the sample over time, even in the timeframe required for image capture. Sensitivity and specificity to target molecules (e.g., DNA) is also a limiting factor in traditional staining methodologies. For example, the widely used DAPI (4',6-diamidino-2-phenylindole) nuclear counterstain is useful for locating the position and shape of cell nuclei, but does not bind specifically to render interpretable nuclear texture. Other fluorescent dyes used as DNA counterstains and markers include the Hoechst stains (e.g., Hoechst 33258 and Hoechst 33342) and propidium iodide. These materials, however, suffer from photo-induced degradation of photoluminescence intensity and spectral shift.

The existing prior art in the use of fluorescent dyes as DNA counterstains and markers utilizes small molecule organic and inorganic complexes. The application of a nanomaterial-based counterstain system provides a means to overcome the inherent flaws in the use of small molecule fluorophores due to its photostable optical characteristics. Quantum dot nanomaterials have been used mostly to detect DNA using FRET (Fluorescence Resonance Energy Transfer) or PET (Photoinduced Electron Transfer) based systems, (Dubeftret, *Nature Materials* (2005), 4(11): 797-798.) Another application employing nanomaterials is the use of quantum dots conjugated to nucleic acid-based probes that can hybridize to their complementary DNA sequence targets. (Bentolila et al., *Cell Biochemistry and Biophysics* (2006), 45(1):59-70.) The quantum dot acts as a visual reporter to target sequences. However, the application of such a stain is not compatible with the TMPRSS-ERG and HER2 FISH (fluorescence in situ hybridization) assays because a labeled DNA probe that can bind generally to DNA molecules may hybridize to the target gene, thereby preventing hybridization of the target gene probe and masking the presence of the target gene. The use of quantum dots with DNA interacting molecules to stain nuclear DNA in fixed cells and tissue has not been reported in the scientific literature.

SUMMARY

Embodiments of nanoparticle/DNA-binding moiety conjugates and methods for using the conjugates to visualize a nucleus are disclosed. Kits for performing the method also are disclosed.

Embodiments of the conjugate include a nanoparticle (e.g., a quantum dot, a metal nanoparticle, a metal oxide nanoparticle, a transition metal complex nanoparticle) and a DNA-binding moiety comprising a DNA-binding molecule. Particular disclosed embodiments concern a conjugate comprising a quantum dot and a DNA-binding moiety comprising a DNA-binding molecule. The DNA-binding molecule may be a minor groove binder, a major groove binder, a DNA intercalator, a DNA alkylating agent, or a combination thereof. In some embodiments, the DNA-binding molecule is 4',6-diamidino-2-phenylindole (DAPI), his-benzimide dyes, psoralen, or naphthalene diimide.

In some embodiments, the DNA-binding moiety further includes a linker (e.g., an aliphatic chain or polyalkylene glycol) such that the conjugate has the structure nanoparticle-linker-DNA-binding molecule. In particular disclosed embodiments, the conjugate has the structure quantum dot-linker-DNA-binding molecule. In particular embodiments, the DNA-binding moiety includes a multi-functional linker and a plurality of minor groove binders, DNA intercalators, DNA alkylating agents, or a combination thereof. For example, the multi-functional linker may comprise two polyethylene glycol chains bonded to an N-hydroxysuccinimide ester, and a DNA binding molecule is bound to each polyethylene glycol chain. In particular embodiments, the DNA-binding moiety is selected from

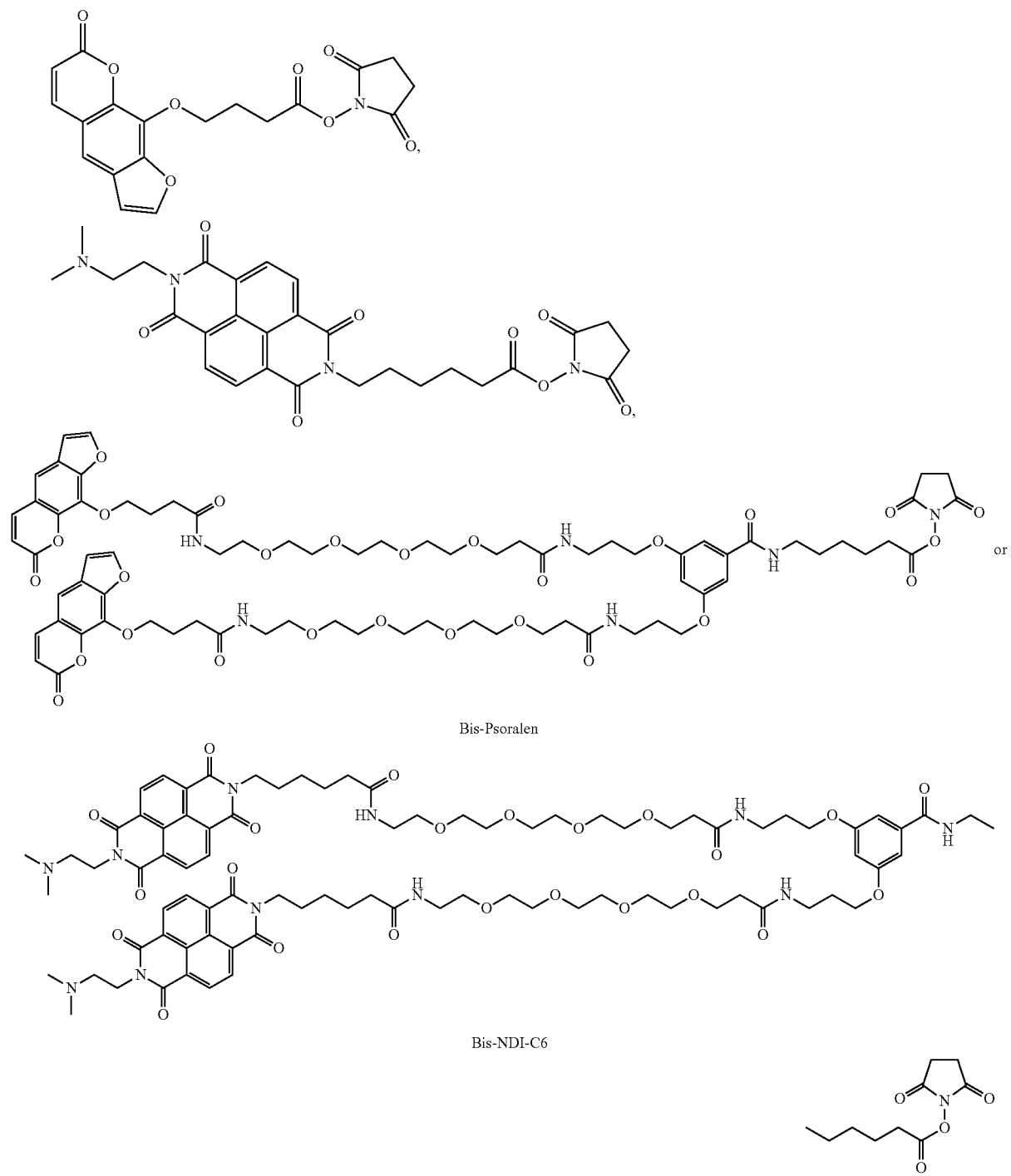

The nucleus is visualized by pretreating a tissue sample, such as a fixed tissue sample, with a protease to permeabilize the nucleus, and then incubating pretreated tissue sample with a nanoparticle/DNA-binding molecule conjugate. The conjugate enters a nucleus and binds to DNA in the nucleus. The nanoparticle then is visualized, thereby visualizing the nucleus. In some embodiments, the nanoparticle is a quantum dot, and the quantum dot fluorescence is detected to visualize the nucleus.

The conjugate is incubated with the tissue sample at a concentration of at least 5 nM, such as at least 25 nM or at least 50 nM. An image is obtained of the nucleus when the nanoparticle is visualized, and computer and image analysis techniques can be used to quantitatively measure nuclear features such as chromosomal distribution, ploidy, shape, size, texture features (e.g., surface area), contextual features (e.g., distance to nuclear boundary), and combinations thereof.

In certain embodiments, one or more additional procedures are performed on the tissue sample. For example, one or probes capable of hybridizing to one or more targets within the tissue sample may be applied to the tissue sample and detected. In some instances, the hybridized probe is detected by visualizing a quantum dot associated with the probe. If the nanoparticle/DNA-binding molecule conjugate includes a quantum dot, the probe's quantum dot is selected to emit fluorescence at a different wavelength than the conjugate's quantum dot. In particular embodiments, the additional procedure is a fluorescence in situ hybridization procedure.

Kits for performing embodiments of the method include a protease enzyme composition, a nanoparticle/DNA-binding molecule conjugate, and a reaction buffer. The protease enzyme composition includes a protease enzyme in a buffer having a salt concentration and pH sufficient to allow the protease enzyme to exhibit proteolytic activity. The reaction buffer has a salt concentration and pH sufficient to enable the conjugate to enter a nucleus within a tissue sample pretreated with the protease enzyme composition.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

In general, the present disclosure concerns an improved system and method for rendering and measuring nuclear characteristics in fluorescence microscopy. Of particular interest is the ability to render nuclear texture in a manner that has previously only been possible in bright-field modalities. Furthermore, embodiments of the disclosed system and method do not interfere with additional staining protocols, thereby enabling the contemporary measurement of multiple sources of information from the same tissue.

Nuclear texture measurements may be broadly classified into the following areas: 1) descriptive statistics of chromatin distribution 2) discrete texture features; 3) range extrema; 4) markovian; 5) run length and 6) fractal texture features. All of these approaches require high staining sensitivity, specificity and contrast of the chromatin (heterochromatin and euchromatin) pattern within the cell nucleus. These methods measure and describe the manner in which image intensity varies with spatial distribution. For example, relatively uniform nuclear staining, such as DAPI, results in little or no textural information whereas a bright-field Thionin Feulgen stain results in a high level of textural information that may be used to discriminate between normal and abnormal pathology.

A further desirable property of a staining methodology for nuclear interrogation is stoichiometry, which pertains to a direct correlation between DNA content and staining intensity. Stoichiometry allows for robust ploidy analysis whereby abnormal chromosome sets are detectable. A failing of traditional fluorescence nuclear counterstains such as DAPI is that they are not inherently stoichiometric and even fade under photobleaching conditions, further decoupling the correlation between target molecules and image intensity.

Figure 1:
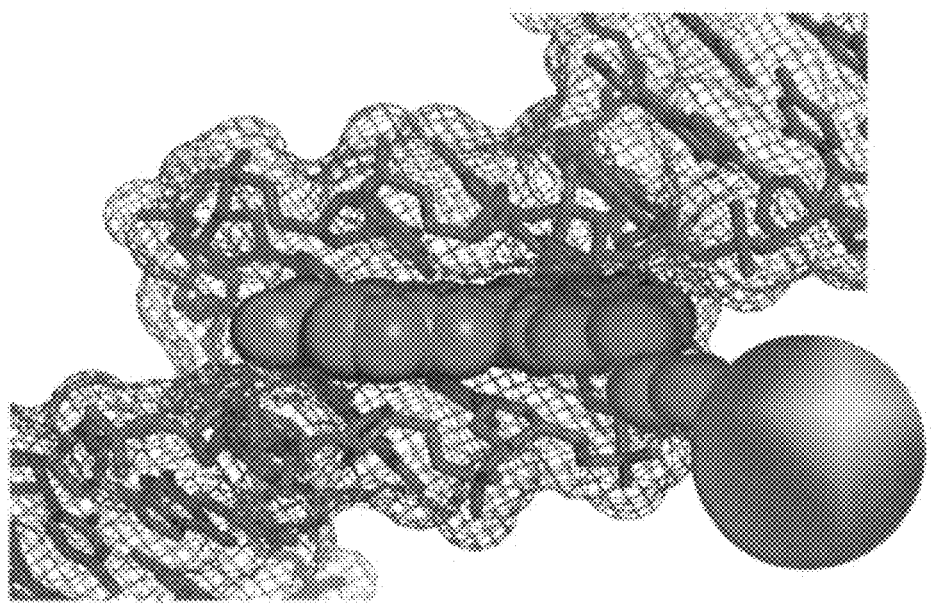
FIG. 1 is a schematic diagram of a DNA-binding moiety-quantum dot conjugate bound to DNA.
Figure 2:
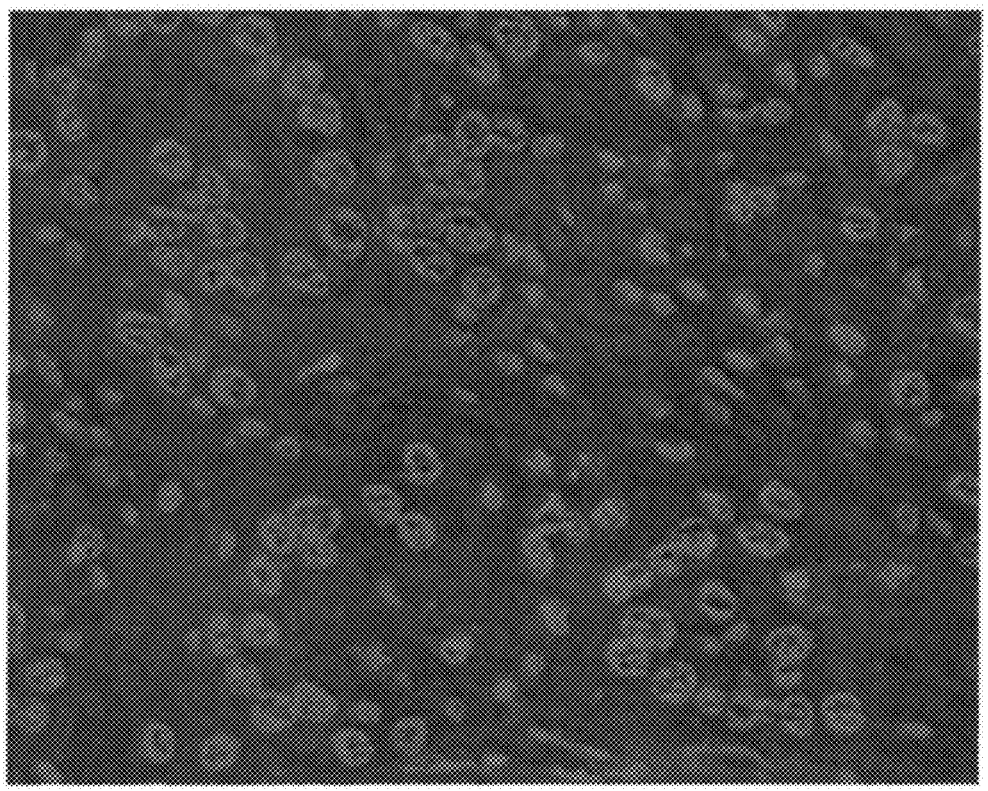
FIG. 2 is a color photograph, using a DAPI filter, of one embodiment of a DNA-binding moiety-quantum dot conjugate used to counterstain prostate tissue nuclei.

The present disclosure provides a combination of optical reporters and DNA interacting probes that allow preferential visualization and measurement of DNA structure and content. Embodiments of DNA-binding moieties conjugated to nanomaterials are disclosed. The DNA-binding moieties comprise at least one DNA-binding molecule. The DNA-binding molecules are capable of directing and binding the nanomaterials to DNA in cell nuclei. FIG. 1 is a schematic diagram depicting a DNA-binding moiety and its conjugated nanomaterial (e.g., a quantum dot) bound to DNA. Also disclosed are embodiments of a method for using the DNA-binding moiety/nanomaterial conjugates to define the nucleus, delineate its boundary, and establish its morphology in a cell. FIG. 2 is a DAPI filter image of a DNA-binding moiety/nanomaterial conjugate used to counterstain prostate tissue nuclei.

Embodiments of the disclosed nanomaterials, e.g., quantum dots, and DNA binding moieties, provide a means to fluorescently define and delineate the nuclei in tissue. Quantum dots provide a photostable fluorescent signal. Due to the photostable emission, broad-range absorption spectra (quantum dot absorption spectra span the upper and lower ultraviolet regions and can extend into the visible region, depending upon the size of the quantum dots), and high quantum yields (e.g., >30%, >50%, or even >80%), quantum dots are superior fluorophores compared to their small molecule counterparts. This allows fluorescent staining of nuclei in tissue in conjunction with FISH assays such as the fluorescent HER2 and TMPRSS2-ERG assays.

DNA-binding molecules are organic, inorganic, and transitional metal complexes that bind to DNA via major and/or minor groove binding, intercalation, phosphate backbone binding, and/or DNA alkylation. The different DNA-binding agents each direct the nanomaterial to the DNA, but the particular affinity of each DNA-binding agent determines the staining profile of the DNA in the nucleus. The repertoire of DNA-binding agents allows high molecular selectivity and regioselectivity.

I. TERMS AND DEFINITIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021629); and Robert A. Meyers (ed.), *Molecular Biology and Biotechnology: a Comprehensive Desk Reference*, published by Wiley, John & Sons, Inc., 1995 (ISBN 0471186341); and other similar references. Definitions of common terms in chemistry may be found, for example, in Richard J. Lewis, Sr. (ed.), *Hawley's Condensed Chemical Dictionary*, published by John Wiley & Sons, Inc., 1997 (ISBN 0-471-29205-2).

In order to facilitate review of the various embodiments of the disclosure, the following explanations of specific terms are provided:

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic groups can either be unsubstituted or substituted. An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group). Exemplary aliphatic substituents include, for instance, amine, amide, sulfonamide, halogen, cyano, carboxy, hydroxy, mercapto, trifluoromethyl, alkyl, alkoxy, alkylthio, thioalkoxy, arylalkyl, heteroaryl, alkylamino, dialkylamino, or other functionality.

Aromatic or aryl compounds typically are unsaturated, cyclic hydrocarbons having alternate single and double bonds. Benzene, a 6-carbon ring containing three double bonds, is a typical aromatic compound.

Bis is a prefix meaning "twice" or "again." It is used in chemical nomenclature to indicate that a chemical group or radical occurs twice in a molecule. For example, a bis-ester has two ester groups.

Combilexin: A molecule combining a sequence-specific, minor-groove-binding polyamide chain with an intercalator.

Conjugate: A compound having a nanoparticle, such as a quantum dot, and a molecule effectively coupled to the nanoparticle, either directly or indirectly, by any suitable means. For example, the molecule can be covalently or noncovalently electrostatically) coupled to the nanoparticle. Indirect attachment of the molecule to the nanoparticle also is possible, such as by using a "linker," so long as the linker does not negatively affect the luminescence of the quantum dot or the function of the molecule. Molecular linkers known in the art include aliphatic compounds, alkylene oxides, primary amines, thiols, streptavidin, neutravidin, biotin, or similar compounds.

Conjugating, joining, bonding or linking: Coupling a first unit to a second unit. This includes, but is not limited to, covalently bonding one molecule to another molecule, non-covalently bonding one molecule to another (e.g., electrostatically bonding) (see, for example, U.S. Pat. No. 6,921,496, which discloses methods for electrostatic conjugation), non-covalently bonding one molecule to another molecule by hydrogen bonding, non-covalently bonding one molecule to another molecule by van der Waals forces, and any and all combinations of such couplings.

Counterstaining is a method of post-treating samples after they have already been stained with agents to detect one or more targets, such that their structures can be more readily visualized under a microscope. For example, a counterstain is optionally used prior to coverslipping to render an immunohistochemical stain more distinct. Counterstains differ in color from a primary stain. Numerous counterstains are well known, such as hematoxylin, eosin, methyl green, methylene blue, Giemsa, Alcian blue, DAPI, and Nuclear Fast Red. In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing, desired attribute. For example, toluidine blue, DAPI, and pontamine sky blue can be mixed together to form a counterstain.

Detect: To determine if an agent (such as a signal or particular antigen, protein or nucleic acid) is present or absent, for example, in a sample. In some examples, this can further include quantification, and/or localization, for example localization within a cell or particular cellular compartment. "Detecting" refers to any method of determining if something exists, or does not exist, such as determining if a target molecule is present in a biological sample. For example, "detecting" can include using a visual or a mechanical device to determine if a sample displays a specific characteristic. In certain examples, detection refers to visually observing a probe bound to a target, or observing that a probe does not bind to a target. For example, light microscopy and other microscopic means are commonly used to detect chromogenic precipitates fix methods described here.

Emission or emission signal: The light of a particular wavelength generated from a source. In particular examples, an emission signal is emitted from a fluorophore after the fluorophore absorbs light at its excitation wavelength(s).

Excitation or excitation signal: The light of a particular wavelength necessary and/or sufficient to excite an electron transition to a higher energy level. In particular examples, an excitation is the light of a particular wavelength necessary and/or sufficient to excite a fluorophore to a state such that the fluorophore will emit a different (such as a longer) wavelength of light than the wavelength of light from the excitation signal.

Fluorescence is the emission of visible radiation by an atom or molecule passing from a higher to a lower electronic state, wherein the time interval between absorption and emission of energy is $10^{-8}$ to $10^{-3}$ second. Fluorescence occurs when the atom or molecule absorbs energy from an excitation source (e.g., an ultraviolet lamp) and then emits the energy as visible radiation.

Fluorescence it situ hybridization (FISH): FISH is a technique used to detect and localize the presence or absence of specific DNA sequences on chromosomes. FISH uses fluorescent probes that bind to only those parts of the chromosome with which they show a high degree of sequence similarity. FISH also can be used to detect particular mRNA sequences within tissue samples.

A functional group is a specific group of atoms within a molecule that is responsible for the characteristic chemical reactions of the molecule. Exemplary functional groups include, without limitation, alkane, alkene, alkyne, arene, halo (fluoro, chloro, bromo, iodo), epoxide, hydroxyl, carbonyl (ketone), aldehyde, carbonate ester, carboxylate, ether, ester, peroxy, hydroperoxy, carboxamide, amine (primary, secondary, tertiary), ammonium, imide, azide, cyanate, isocyanate, thiocyanate, nitrate, nitrite, nitrile, nitroalkane, nitroso, pyridyl, phosphate, sulfonyl, sulfide, thiol (sulfhydryl), disulfide.

Heteroaryl compounds are aromatic compounds having at least one heteroatom, i.e., one or more carbon atoms in the ring has been replaced with an atom having at least one lone pair of electrons, typically nitrogen, oxygen, or sulfur.

Intercalation: A term referring to the insertion of a material (e.g., an ion or molecule) into the microstructure of another material. For example, psoralen can insert, or intercalate, into the minor groove of a double-stranded DNA helix.

Lexitropsin: A member of an analog family of the natural antibiotics netropsin and distamycin.

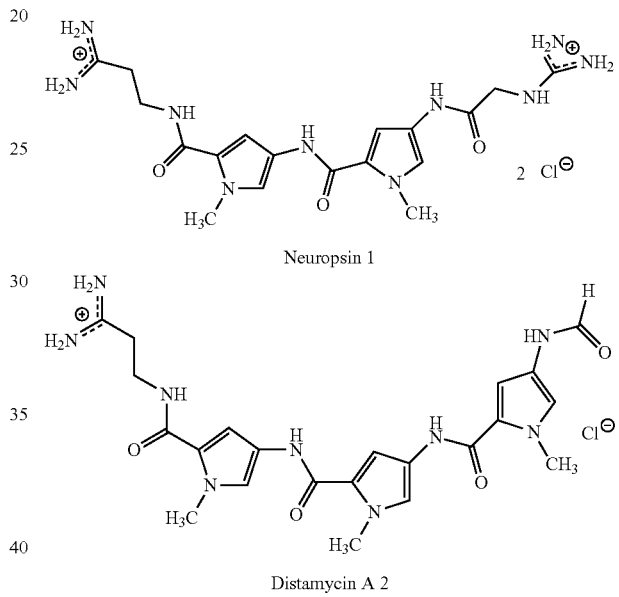

Neuropsin 1

Distamycin A 2

Linker: A molecule or group of atoms positioned between two moieties. For example, a quantum dot-DNA-binding moiety conjugate may include a linker between the quantum dot and a DNA-binding molecule. Typically, linkers are bifunctional, the linker includes a functional group at each end, wherein the functional groups are used to couple the linker to the two moieties. The two functional groups may be the same, i.e., homobifunctional linker, or different, i.e., a heterobifunctional linker.

Moiety: A moiety is as fragment of a molecule, or a portion of a conjugate.

Multiplex, -ed, -ing: Detection of multiple targets in a sample substantially simultaneously, or sequentially, as desired, using plural different conjugates. Multiplexing can include identifying anti/or quantifying nucleic acids generally, DNA, RNA, peptides, proteins, both individually and in any and all combinations. Multiplexing also can include detecting two or more of a gene, a messenger and a protein in a cell in its anatomic context.

Nanomaterial: A material with morphological features and/or special properties derived from its nanoscale dimensions (i.e., having one dimension that is less than 100 nm). Nanomaterials typically are comprised of nanoparticles. Nanoparticles of a given material may have very different properties compared to larger particles of the same material. For example, opaque substances may become transparent (e.g., copper), inert materials may become catalytic (e.g., platinum, gold), stable materials (e.g., aluminum) may become combustible, insulators may become conductors (e.g., silicon), etc.

Nanoparticle: A nanoscale particle with a size that is measured in nanometers, for example, a nanoscopic particle that has at least one dimension of less than 100 nm. Examples of nanoparticles include paramagnetic nanoparticles, superparamagnetic nanoparticles, metal nanoparticles, metalloid nanoparticles, metal oxide nanoparticles, fullerene-like materials, inorganic nanotubes, dendrimers (such as with covalently attached metal chelates), nanofibers, nanohorns, nano-onions, nanorods, nanoprisms, nanoropes and quantum dots. A nanoparticle can produce a detectable signal, for example, through absorption and/or emission of photons (including radio frequency and visible photons) and plasmon resonance.

Peptide nucleic acid: An artificial polymer comprising a backbone of repeating N-(2-aminoethyl)glycine units linked by peptide bones. Various purine and pyrimidine bases, B, are linked to the backbone by methylene carbonyl bonds.

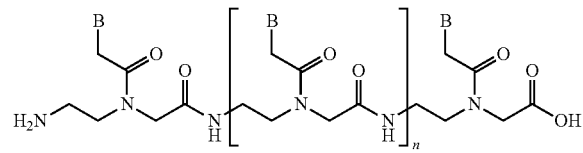

Photobleach: To become less absorbent, reflective or fluorescent upon exposure to light; to become bleached or faded by exposure to light. Photobleaching refers to the photochemical degradation or destruction of a fluorophore.

Photostable: Stable towards photochemical change. As used herein, photostable means that the detectable signal does not diminish over time when exposed to light.

Probe: An isolated nucleic acid, an isolated synthetic oligonucleotide, attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (in Molecular Cloning: A Laboratory Manual, CSHL, New York, 1989) and Ausubel et al. (In Current Protocols in Molecular Biology, Greene Publ. Assoc, and Wiley-Intersciences, 1992).

One of ordinary skill in the art will appreciate that the specificity of a particular probe increases with its length. Thus, probes can be selected to provide a desired specificity, and may comprise at least 17, 20, 23, 25, 30, 35, 40, 45, 50 or more consecutive nucleotides of desired nucleotide sequence. In particular examples, probes can be at least 100, 250, 500, 600 or 1000 consecutive nucleic acids of a desired nucleotide sequence.

Quantum dot: A nanoscale particle that exhibits size-dependent electronic and optical properties due to quantum confinement. Quantum dots have, for example, been constructed of semiconductor materials (e.g., cadmium selenide and lead sulfide) and from crystallites (grown via molecular beam epitaxy), etc. A variety of quantum dots having various surface chemistries and fluorescence characteristics are commercially available from Invitrogen Corporation, Eugene, Oreg. (see, for example, U.S. Pat. Nos. 6,815,064, 6,682,596 and 6,649,138, each of which patents is incorporated by reference herein). Quantum dots are also commercially available from Evident Technologies (Troy, N.Y.). Other quantum dots include alloy quantum dots such as ZnSSe, ZnSeTe, ZnSTe, CdSSe, CdSeTe, ScSTe, HgSSe, HgSeTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, InGaAs, GaAlAs, and InGaN quantum dots (alloy quantum dots and methods for making the same are disclosed, for example, in US Publication No 2005/0012182 and PCT Publication WO 2005/001889).

Sample: The term "sample" refers to any liquid, semi-solid or solid substance (or material) in or on which a target can be present. In particular, a sample can be a biological sample or a sample obtained from a biological material. Examples of biological samples include tissue samples and cytology samples. In some examples, the biological sample is obtained from an animal subject, such as a human subject. A biological sample is any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In some examples, a biological sample is bacterial cytoplasm. In other examples, a sample is a test sample. For example, a test sample is a cell, a tissue or cell pellet section prepared from a biological sample obtained from a subject. In are example, the subject one that is at risk or has acquired a particular condition or disease.

Stain: Any biological or chemical entity which, when applied to targeted molecules in biological sample, renders the molecules detectable under microscopic examination. Stains include, without limitation, detectable nucleic acid probes, antibodies, dyes and other reagents which in combination or by themselves result in a colored end product (by bright field or fluorescence detection methodologies). A counterstain is a stain of a contrasting color, or a stain applied to render the effects of another stain more discernible.

Tissue: A collection of interconnected cells that perform a similar function within an organism. Any collection of cells that can be mounted on a standard glass microscope slide including, without limitation, sections of organs, tumor sections, bodily fluids, smears, frozen sections, cytology preps, and cell lines.

II. NANOMATERIALS

Nanomaterials, such as quantum dots, nanocrystals, and nanoparticles, provide unique advantages over their small molecule fluorophore counterparts due to their structuraland chemical-dependent electronic and optical properties. Nanomaterials such as semiconducting nanocrystals possess optical properties such as broad spectrum optical absorption, a large Stokes shift, narrow emission spectra, and/or photostable high quantum yields. This allows the nanomaterials to be excellent optical reporters. Due to the narrow emission spectra, nanocrystals can be differentiated by their optical signatures and can be used in multiplexing fluorescent assays with little to no convolution of photoluminescent signal. The spectral range of the signal can range from the UV and into the near-IR.

Suitable nanomaterials include quantum dots, metal nanoparticles, and metal oxide nanoparticles. For example, metal nanoparticles provide an optical counterstain of the nuclear DNA in bright-field microscopy. Suitable metals include, but are not limited to, gold, silver, palladium, platinum, and transition metal alloys (e.g., Au/Ag). Transition metal complex-based nanomaterials, e.g., Prussian blue-type nanoparticles, also are suitable. Prussian blue-type metal complexes typically comprise a 3-dimensional crystal structure including two kinds of metal atoms in a NaCl-type lattice cross-linked with cyano groups (see, e.g., U.S. Patent Publication No. 2010/0133487); exemplary metals include vanadium, chromium, molybdenum, tungsten, manganese, iron, ruthenium, cobalt, nickel, platinum, and copper. Metal oxide nanoparticles, including alumina, silica, and titanic may be suitable. Metal oxide nanoparticles doped with fluorescent lanthanides also can be used in fluorescent imaging, but are not suitable for bright field imaging. All of these materials can be modified to carry the DNA-binding moieties and employed to detect and stain nuclear DNA.

Quantum dots are semiconductor nanocrystalline particles, and without limiting the present invention to use with particle light emitters of a particular size, typically measure 2-10 nm in size. Quantum dots typically are stable fluorophores, often are resistant to photo bleaching, and have a wide range of excitation, wavelength and narrow emission spectra. Quantum dots having particular emission characteristics, such as emissions at particular wavelengths, can be selected such that plural different quantum dots having plural different emission characteristics can be used to identify plural different targets.

In some embodiments, quantum dots are protected by an electrostatically bound shell of trioctyl phosphine oxide (TOPO) and an intercalating amphiphilic polymer to induce water solubility. This polymer has approximately 30 terminal amine groups for further functionalization. See E. W. Williams, et al, "Surface-Modified Semiconductive and Metallic Nanoparticles Having Enhanced Dispersibility in Aqueous Media", U.S. Pat. No. 6,649,138 (incorporated by reference, herein). The terminal amine groups can be used to conjugate the quantum dot to a DNA-binding moiety.

Quantum dot conjugates are characterized by quantum yields comparable to the brightest traditional dyes available. Additionally, these quantum dot-based fluorophores absorb 10-1000 times more light than traditional dyes. Emission from the quantum dots is narrow and symmetric, which means overlap with other colors is minimized, resulting in minimal bleed through into adjacent detection channels and attenuated crosstalk, in spite of the fact that many more colors can be used simultaneously. Symmetrical and tunable emission spectra can be varied according to the size and material composition of the particles, which allows flexible and close spacing of different quantum dots without substantial spectral overlap. In addition, their absorption spectra are broad, which makes it possible to excite all quantum dot color variants simultaneously using a single excitation wavelength, thereby minimizing sample autofluorescence.

Standard fluorescence microscopes are an inexpensive tool for the detection of quantum dot conjugates. Since quantum dot conjugates are virtually photo-stable, time can be taken with the microscope to find regions of interest and adequately focus on the samples.

III. DNA-INTERACTING MOLECULES

The ability to direct a nanomaterial to nuclear DNA is provided by conjugating the nanomaterial (e.g., a quantum dot) to a small molecule that is capable of interacting with DNA. The small molecules that target and direct the nanomaterials to DNA can be organic molecules, inorganic molecules, or transition metal complexes. These agents interact with DNA through hydrogen bonding, electrostatic interactions, van der Waals forces, and/or covalent bonding. They can be further classified into categories based upon their regioselectivity for DNA, such as minor and major groove binders, phosphate backbone binders, intercalators, and base modifiers/alkylating agents. Exemplary small molecules include, but are not limited to, DNA groove binders such as DAPI and Hoechst dye; intercalators such as psoralen, naphthalene diimide, and SYBR101 (a fluorescent dye, available from Invitrogen Corporation), and DNA base modifiers such as psoralen. Some DNA-interacting molecules interact through a combination of mechanisms, i.e., minor groove binding and intercalation, intercalation and alkylation, and other combinations. Exemplary molecules include lexitropsins, combilexins, peptide nucleic acids, and topoisomerase I inhibitors (e.g., indenoisoquinolines). (See, e.g., Pindur et al., *Current Medicinal Chemistry*, 2005, 12:2805-284)

A. Minor Groove Binders

Small molecules that bind to the minor groove of DNA include, but are not limited to, DAN, the Hoechst dyes, distamycin A, netropsin, actinomycin D, lexitropsins, combilexins, N-methyl pyrrole and N-methyl imidazole polyamides. The Hoechst dyes are a family of bis-benzimides. The structure of one Hoechst dye, Hoechst 33342, is shown below:

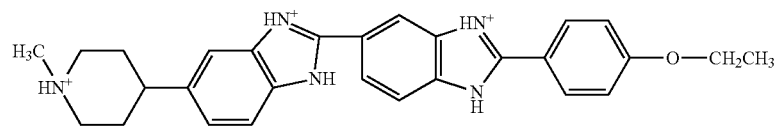

Hoechst 33342

Another common Hoechst dye is Hoechst 33258, which differs from Hoechst 33342 by having a hydrogen in place of the ethyl group.

DAPI, or 4',6-diamidino-2-phenylindole, is another minor groove binder:

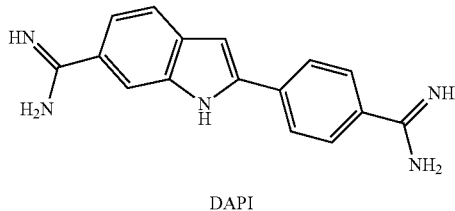 [SMILES: N=C(N)c1ccc(-c2cc3ccc(C(=N)N)cc3[nH]2)cc1]

DAPI

DAPI associates with AT nucleotide clusters in the minor groove of double-stranded DNA, and can be used as a nuclear counterstain. DAPI produces blue fluorescence; however, like other fluorescent dyes, DAPI undergoes photo-induced degradation of photoluminescence intensity over time.

Figure 3A:
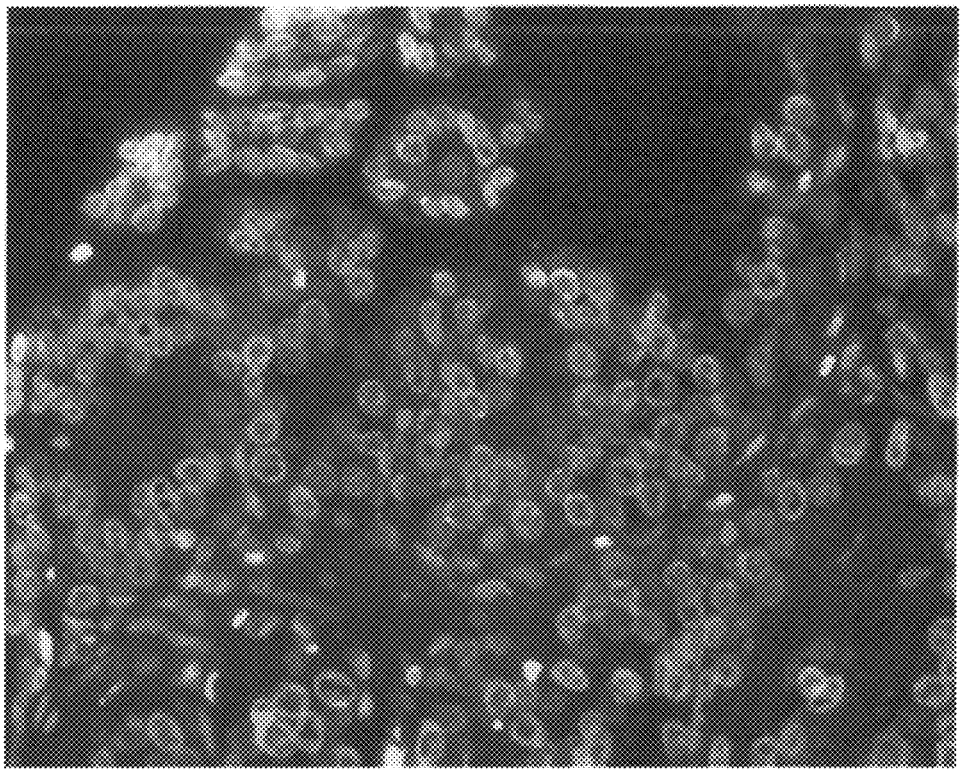
FIGS. 3A-B are photographs of cell nuclei counterstained with a quantum dot-DAPI conjugate (FIG. 3A) and DAPI (FIG. 3B).
Figure 3B:
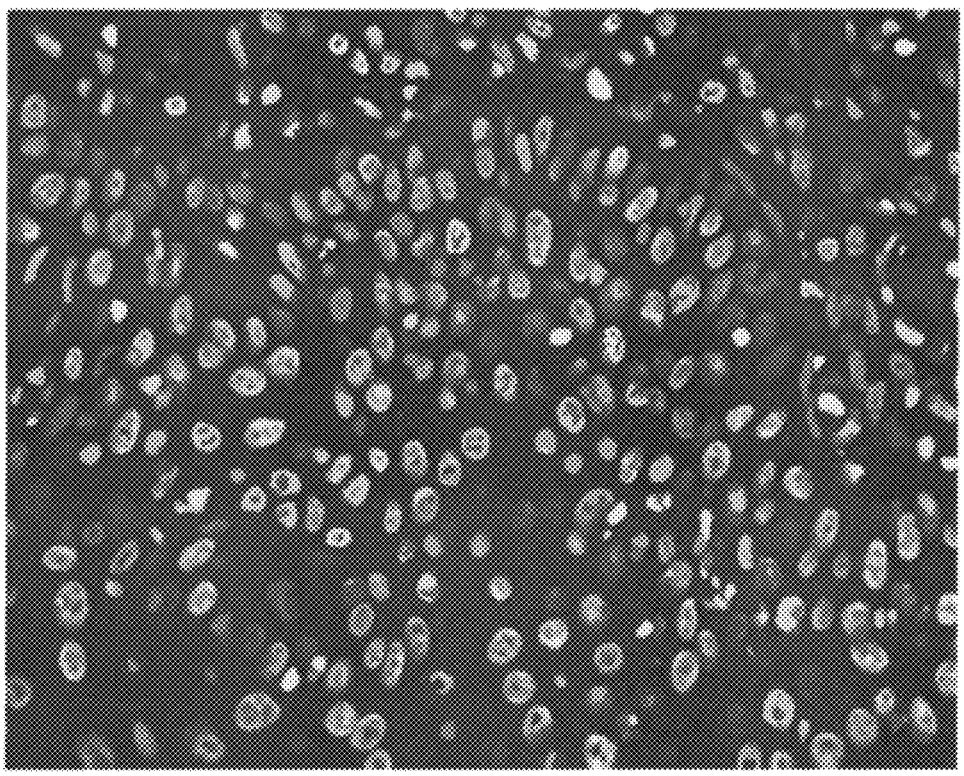

The high affinity of DAPI for the minor groove of DNA can be utilized to direct a quantum dot to nuclear DNA, producing quantum-dot-stained DNA in fixed cells and tissue. Remarkably, the staining pattern and morphology of the nuclei is similar to the staining of DAPI (FIGS. 3A-B). Spectroscopic examination of the staining shows both the succinct optical signal of the quantum dot and the broad signature indicative of the organic dye, DAPI. The advantage of this conjugate is that it provides a nuclear staining and morphology very similar to DAPI while possessing the photostable signal of the quantum dot.

B. DNA Intercalators

Intercalators are molecules that interact with DNA by inserting in between the bases of the double stranded DNA; they are held in position by van der Waal's forces. Exemplary DNA intercalators include, but are not limited to, actinomycin D, combilexins, psoralen and naphthalene diimide (NDI):

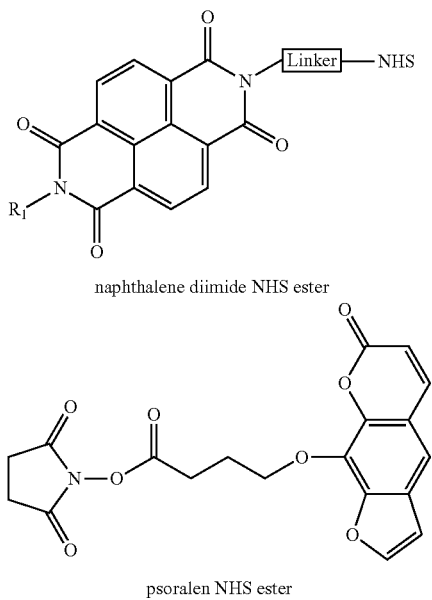

naphthalene diimide NHS ester psoralen NHS ester

Conjugation of quantum dots to these molecules results in nuclear staining. The staining intensity depends, at least in part, upon the particular intercalator and the concentrations of the conjugate applied to the cell or tissue sample.

Figure 4:
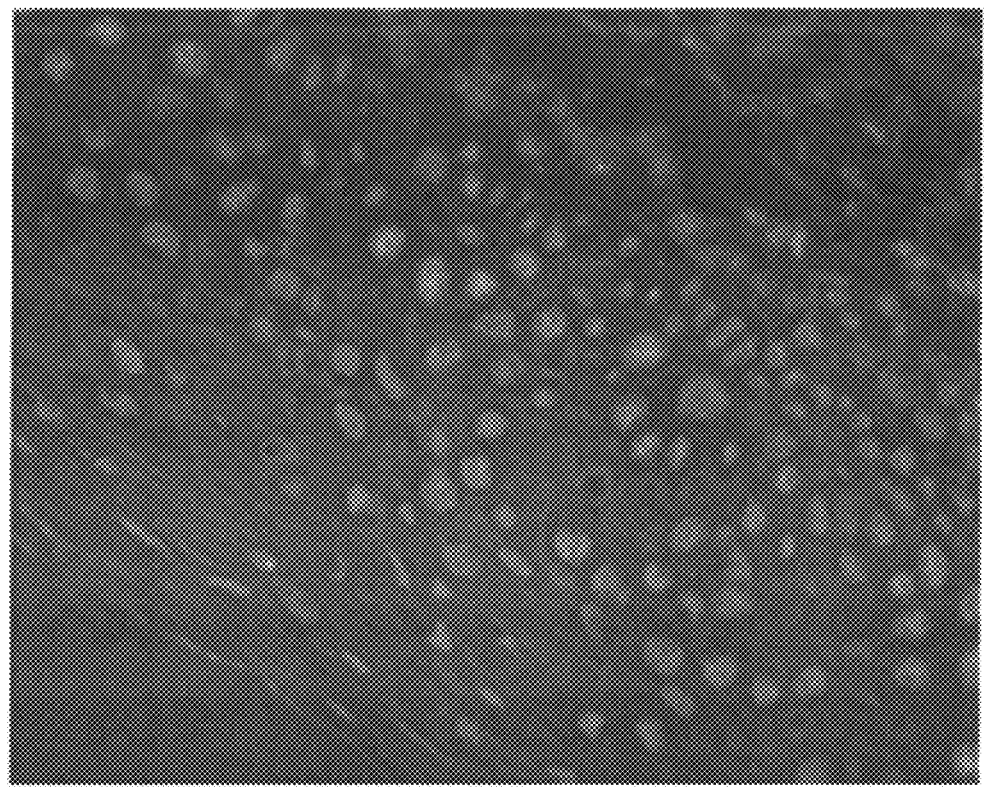
FIG. 4 is a photograph illustrating epithelial tissue nuclei counterstained with a quantum dot-psoralen conjugate (QD490PEG-NH-Psoralen).

Psoralen-quantum dot conjugates demonstrate a high affinity for nuclear DNA in tissue. The staining shows morphological characteristics of the nucleus. At a concentration of 100 nM, the nucleus is dearly delineated from the surrounding tissue (see, e.g., FIG. 4).

Figure 5:
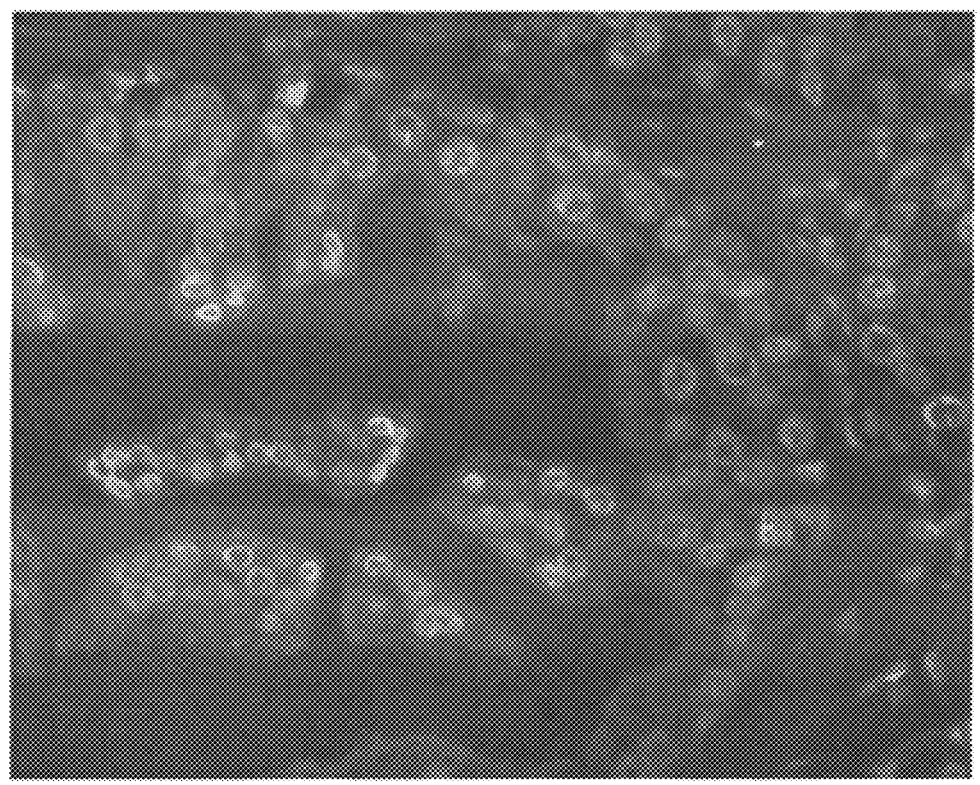
FIG. 5 is a photograph illustrating prostate tissue nuclei counterstained with a quantum dot-naphthalene diimide conjugate (QD490:NDI-C6).

Even greater specificity and affinity for the nuclear DNA is observed when a quantum dot is conjugated to naphthalene diimide. Distinct nuclear delineation and morphology are observed at concentrations of 50 nM and greater (see, e.g., FIG. 5). Concentrations near 25 nM adequately stain the peripheral boundary of the nucleus and show some degree of nuclear morphology. In fact, concentrations as low as 6 nM are capable of staining the nucleus and differentiating it from the surrounding tissue. Thus, quantum dot-naphthalene diimide conjugates are useful for nuclear counterstaining in fixed tissues at concentrations of greater than 5 nM, greater than 20 nM, or greater than 50 nM, such as concentrations ranging from 5 nM to 100 nM, 2.0 nM to 75 nM, or 25 nM to 50 nM.

Figure 6:
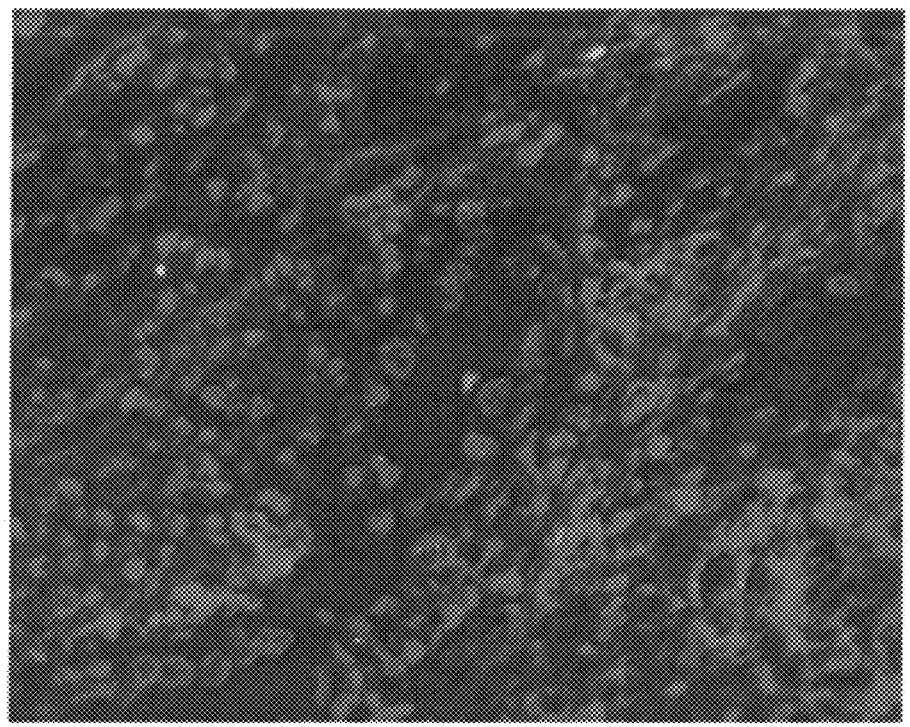
FIG. 6 is a photograph illustrating QD490:NDI-C6 conjugate counterstaining of prostate tissue nuclei in conjunction with a FISH assay utilizing a TMPRSS2 probe containing quantum dots QD565 and QD655.
Figure 7:
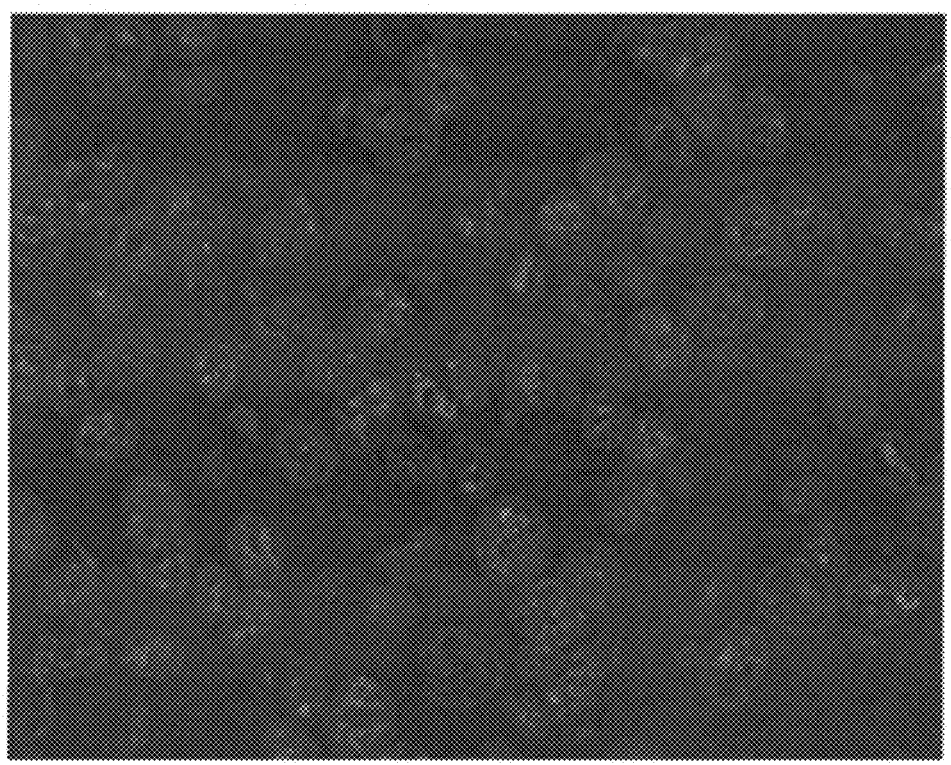
FIG. 7 is a photograph illustrating QD490:NDI-C6 conjugate counterstaining of prostate tissue nuclei in conjunction with a FISH assay utilizing an HER2-CHR17 probe containing quantum dots QD565 and QD655.
Figure 8:
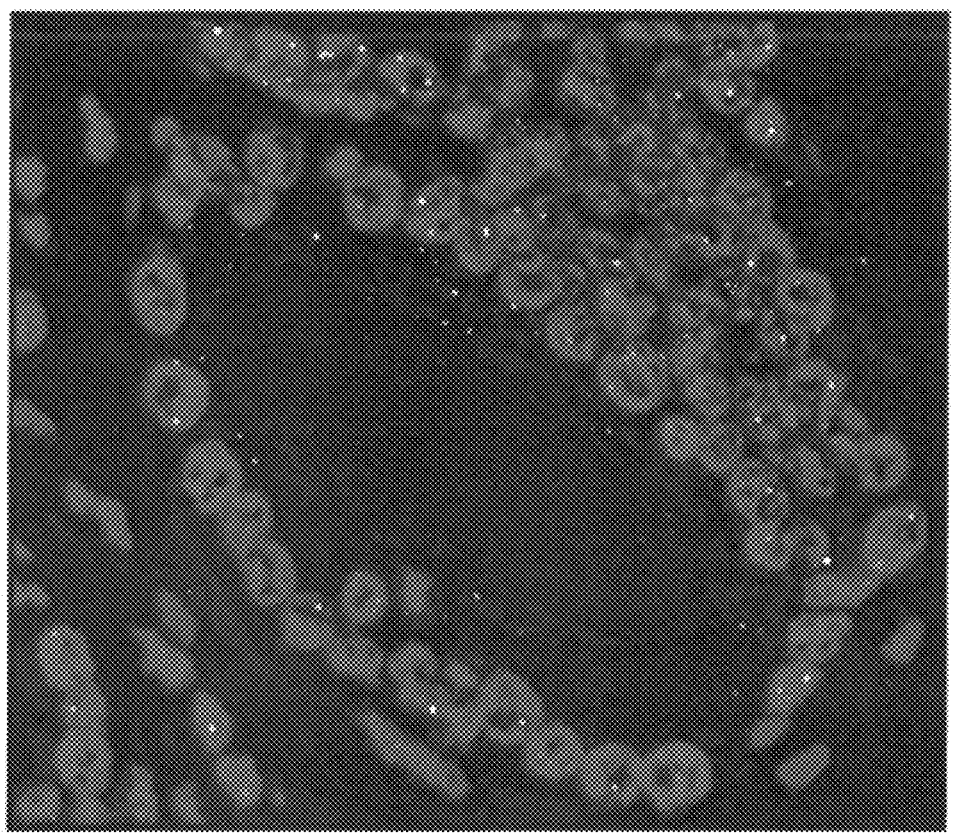
FIG. 8 is a photograph illustrating QD490:NDI-C6 conjugate counterstaining of prostate tissue nuclei in conjunction with a FISH assay utilizing TMPRSS2, SLC45A3, and ETV1 probes conjugated to quantum dots QD565, QD585, QD605, and QD655, respectively.

The quantum does narrow emission spectrum allows use of the nuclear stain in conjunction with other probes utilizing quantum dots that emit fluorescence at different wavelengths. For example, when a quantum dot-naphthalene diimide probe was used to stain prostate tissue at a concentration of 25 nM, quantum dot FISH probes from both the dual color TMPRSS2 (3' 5' ERG) (FIG. 6) and dual color HER2-Chr17 (FIG. 7) fluorescent assays were also visible. This quantum dot conjugate also was used in a FISH assay with four quantum probes TMPRSS2 (3' 5' ERG), ERG, SLC45A3, and ETV1 (FIG. 8). In each of these assays, the DNA stains showed superior performance due to its spectral stability and minimally spectra overlap.

C. DNA Alkylating Agents

Another advantage provided by the psoralen ligand is the ability to covalently bind the quantum dot to the bases of the DNA. Under UV irradiation (i.e., >350 nm), psoralen undergoes a photoinduced 2+2 cycloaddition to the base, thymidine. This process covalently attaches the psoralen-quantum dot conjugate to the DNA. Other DNA binders that are alkylating agents include, but are not limited to, analogs and derivatives of lexitropsins and pyrrole-imidazole-polyamides (such as nitrogen mustards). (Pindur et al.)

IV. PREPARATION OF NANOMATERIAL/DNA-BINDING MOIETY CONJUGATES

Nanomaterials, e.g., quantum dots, and DNA-binding moieties comprising at least one DNA-binding, or targeting, molecule are brought together with standard condensation techniques utilizing activated carboxyl moieties and amines on the nanomaterial and/or the DNA-targeting, molecule. Some DNA-binding molecules can be used without modification to prepare nanomaterial/DNA-binding moiety conjugates. For example, succinimidyl-[4-(psoralen-8-yloxy)] butyrate, a psoralen derivative, is commercially available and can be used without any further modification.

In some embodiments, a DNA-binding moiety is modified to facilitate conjugation to a nanomaterial, such as a quantum dot or a metal nanoparticle. To further facilitate conjugation, the nanomaterial also may be modified to include functional group(s) suitable for conjugation. For example, quantum dots may include an outer functionalized passivating layer comprising amino groups. Metal nanoparticles similarly may include an outer functionalized layer comprising functional groups (e.g., amino, cyano, thiol, carboxyl, etc.) suitable for conjugation to a DNA-binding molecule.

Figure 9:
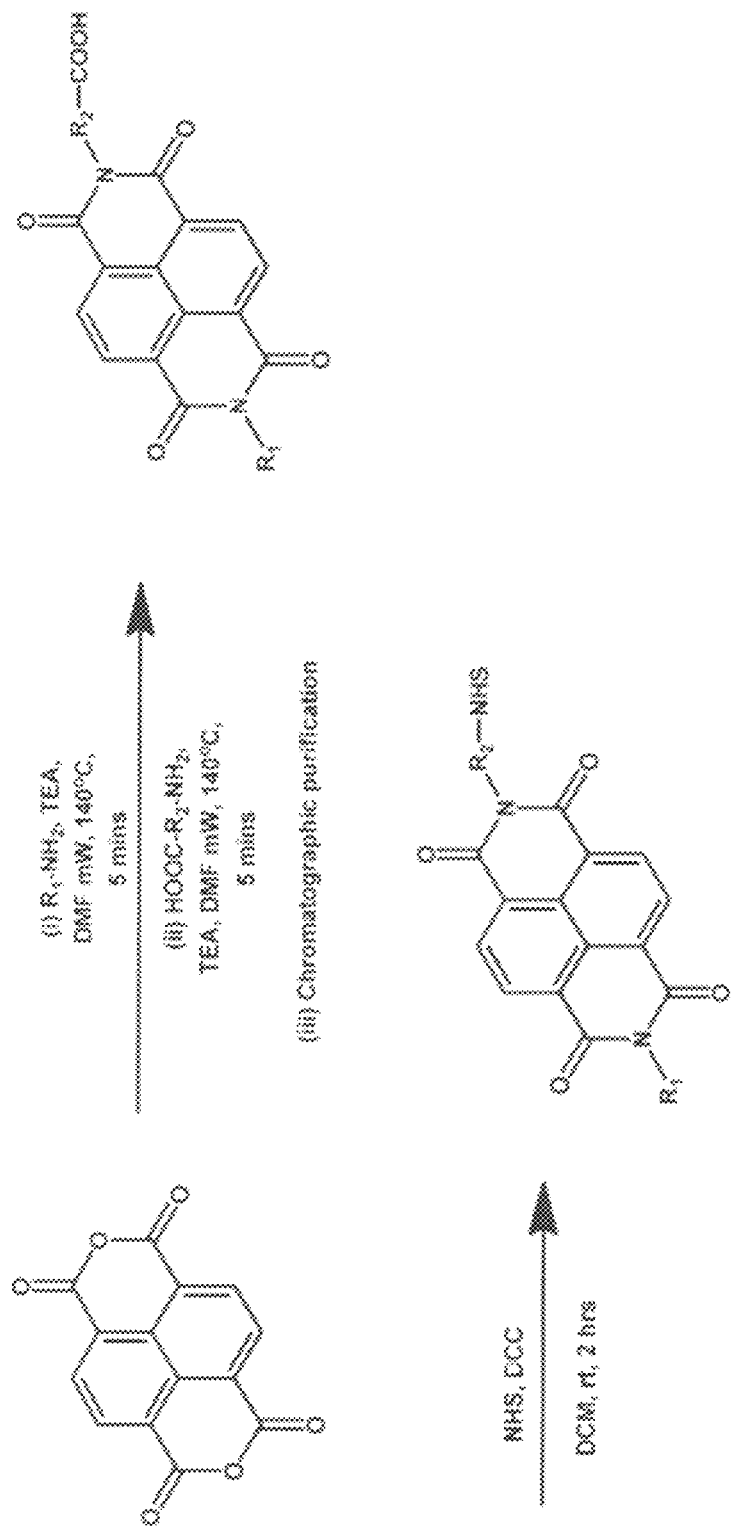
FIG. 9 is a synthetic scheme for adding N-hydroxysuccinimide (NHS) ester moieties to DNA-binding molecules where $R_1$ and $R_2$ independently are substituted or unsubstituted aliphatic, substituted or unsubstituted aromatic, heteroaromatic, or a polyalkylheteroatom chain such as an alkylene oxide chain (e.g., a polyalkylene glycol).

In a particular embodiment, modifying a DNA-binding moiety to include an N-hydroxysuccinimide ester functional group allows conjugation of the DNA-binding molecule to a quantum dot via the NHS ester moiety and an amino group on the quantum dot. FIG. 9 illustrates a general synthetic scheme for adding NHS ester moieties to DNA-binding moieties, e.g., naphthalene diimide. $R_1$ and $R_2$ independently are substituted or unsubstituted aliphatic, substituted or unsubstituted aromatic, heteroaromatic, or a polyalkylheteroatom chain such as an alkylene oxide chain (e.g., a polyalkylene glycol).

The NHS ester moiety can react with a primary amine group on a quantum dot surface, forming a quantum dot-DNA-binding moiety conjugate as shown below where "DBM" represents a DNA-binding moiety and "QD" represents a quantum dot.

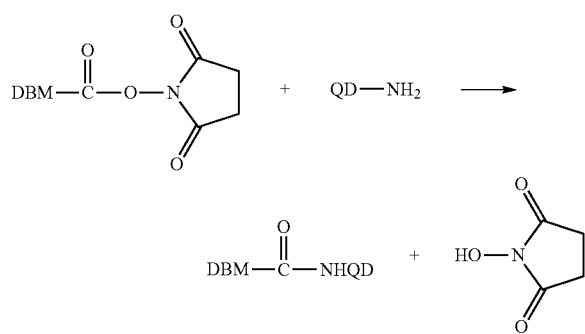

Figure 10:
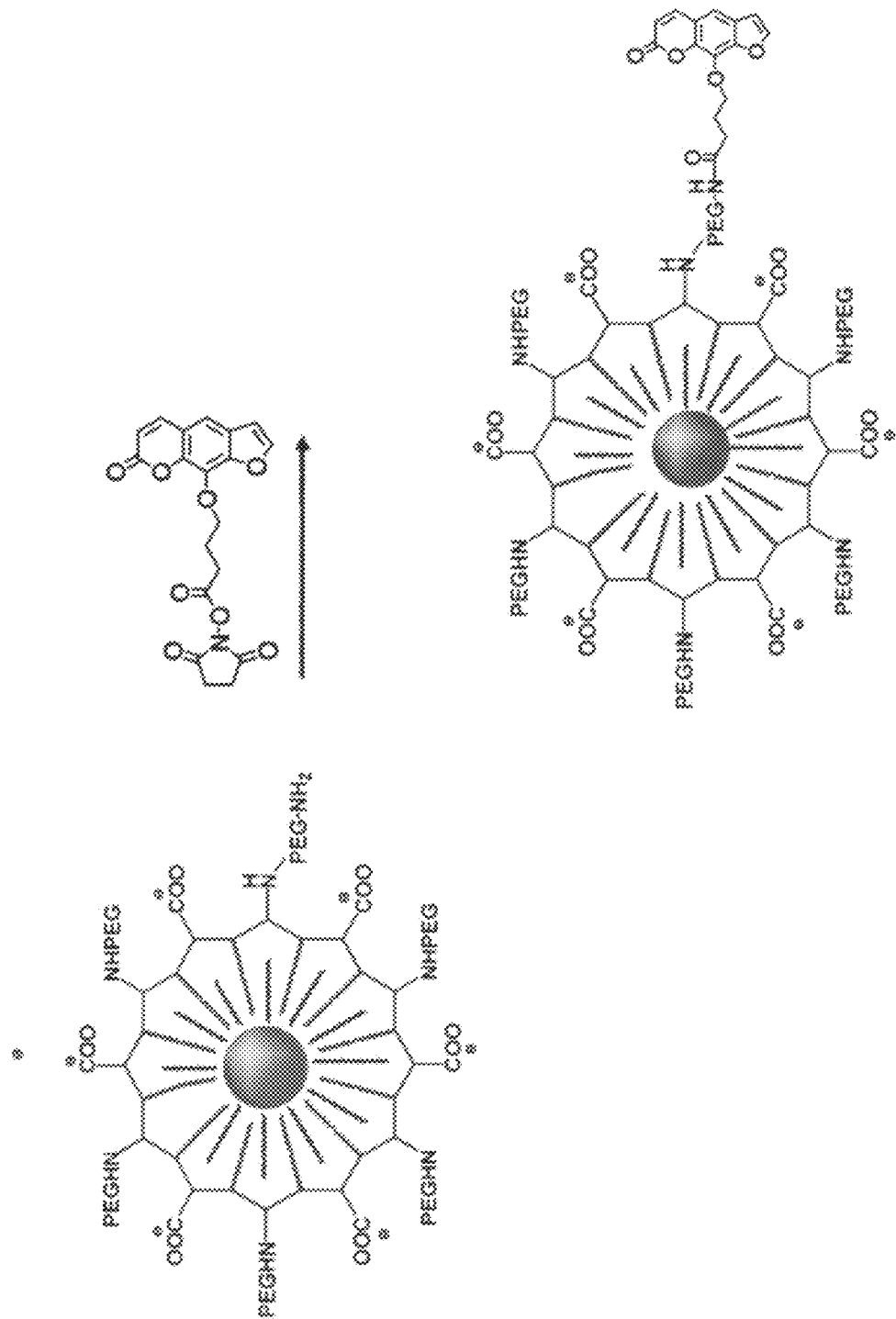
FIG. 10 depicts a reaction between a succinimidyl ester of a DNA-binding moiety and a free amine group on a quantum dot, thereby producing a quantum dot-DNA-binding moiety conjugate.

As shown in FIG. 10, a succinimidyl ester of psoralen can react with a primary amine group on the surface of a quantum dot to provide a quantum dot-psoralen conjugate.

In another embodiment, a DNA-binding moiety may be modified to include a tetrafluorophenyl (TFP) ester moiety. The TFP ester moiety can react with a primary amine group on the quantum dot surface, forming a quantum dot-DNA-binding moiety conjugate.

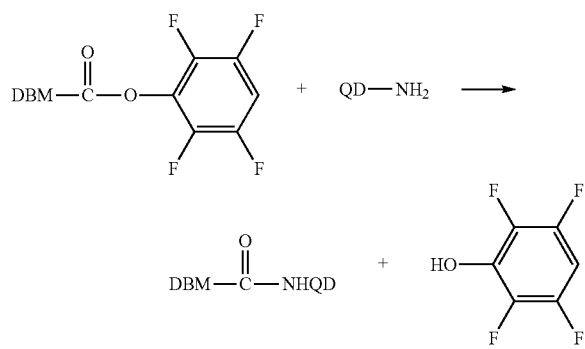

In another embodiment, a DNA-binding moiety may be modified to include a 4-sulfo-2,3,5,6-fluorophenyl (STP) ester moiety. The STP ester moiety can react with a primary amine group on the quantum dot surface, forming a quantum dot-DNA-binding moiety conjugate.

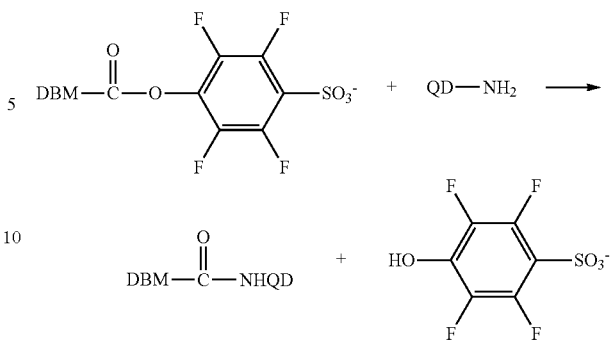

In yet another embodiment, a DNA-binding moiety may be modified to include a sulfonyl chloride moiety. The sulfonyl chloride moiety can react with a primary amine group on the quantum dot surface, forming a quantum dot-DNA-binding moiety conjugate.

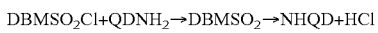

$$DBMSO_2Cl + QDNH_2 \rightarrow DBMSO_2 \rightarrow NHQD + HCl$$

Other chemical transformations that are suitable in an aqueous environment also can be employed, e.g., with NDI-C6 (naphthalene diimide with a C6 linker). Other suitable coupling methods are described, e.g., by Hermanson (*Bioconjugate Techniques*, second edition, May 2, 2008). Purification of conjugates from free DNA interacting molecules can be done with size exclusion chromatography.

In some embodiments, the quantum dot-DNA-binding moiety conjugate includes a linker between the quantum dot and the DNA-binding molecule. The linker provides distance between the quantum dot and the DNA-binding molecule, and may reduce structural constraints, thereby facilitating binding of the conjugate to the DNA. Any linker currently known for this purpose, or developed in the future, can be used to form embodiments of the disclosed conjugates. Useful linkers can either be homo- or heterobifunctional.

A first class of suitable linkers includes aliphatic compounds, such as aliphatic hydrocarbon chains having one or more sites of unsaturation, or alkyl chains. The aliphatic chain also typically includes terminal functional groups that facilitate coupling nanoparticle to a DNA-binding molecule. The length of the chain can vary, but typically has length of 1-30 carbon atoms. However, a person of ordinary skill in the art will appreciate that, if a particular linker has greater than 30 atoms, and still operates efficiently for linking a nanoparticle to a DNA-binding molecule, and the conjugate still functions as desired, then such chain links are within the scope of the present disclosure.

A second class of linkers useful for practicing embodiments of the present disclosure includes alkylene oxides. The alkylene oxides are represented herein by reference to glycols, such as ethylene glycols. In some embodiments, it is useful if the hydrophilicity of the linker is increased relative to the length of its hydrocarbon chain. A person of ordinary skill in the art will appreciate that, as the number of oxygen atoms increases, the hydrophilicity of the compound also may increase. Thus, linkers of the present disclosure may have a formula of (—OCH₂CH₂—), where n is from about 2 to about 15, but more particularly is from about 2 to about 8. Heterobifunctional polyalkyleneglycol linkers that may be useful for practicing certain disclosed embodiments of the present invention are described in U.S. Publication No. 2006/0246524 and U.S. Publication No. 2007/0117153, which are incorporated herein by reference.

Linkers containing psoralen and naphthalene diimide (NDI) (shown below) have been synthesized and conjugated to quantum dots.

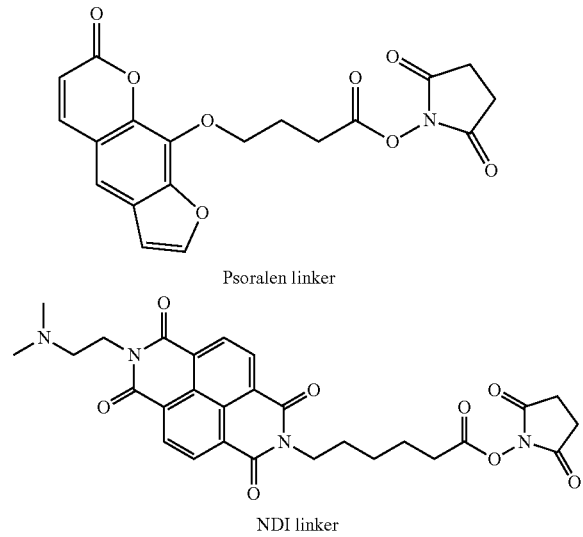

In some embodiments, sensitivity and selectivity of the quantum dot stain is increased through the use of multi-functional branching linkers to which a plurality of DNA-binding molecules are covalently bound. In some embodiments, the linkers are bis-linkers to which two DNA-binding molecules are attached. In certain embodiments, the bis-linker includes two polyethylene glycol chains attached to a common moiety such as an N-hydroxysuccinimide ester. The polyethylenelycol chains have a formula $PEG_n$, where n is 1-50, such as 4 or 8. In a particular embodiment, the linker has the following chemical structure.

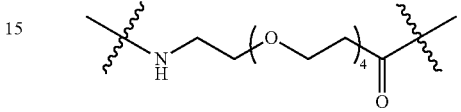

In some embodiments, a quantum dot may be conjugated to the multi-functional linker via a condensation reaction with the N-hydroxysuccinimide moiety of the linker. The branched linkers increase the local concentration of DNA-binding molecules, thereby increasing the affinity to nuclear DNA. Exemplary bis linkers containing psoralen and naphthalene diimide (NDI) have the following structures.

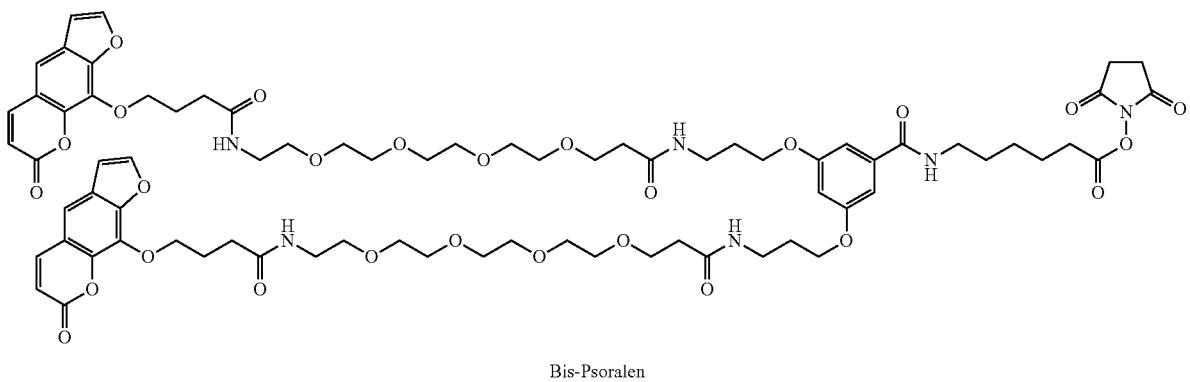

Bis-Psoralen

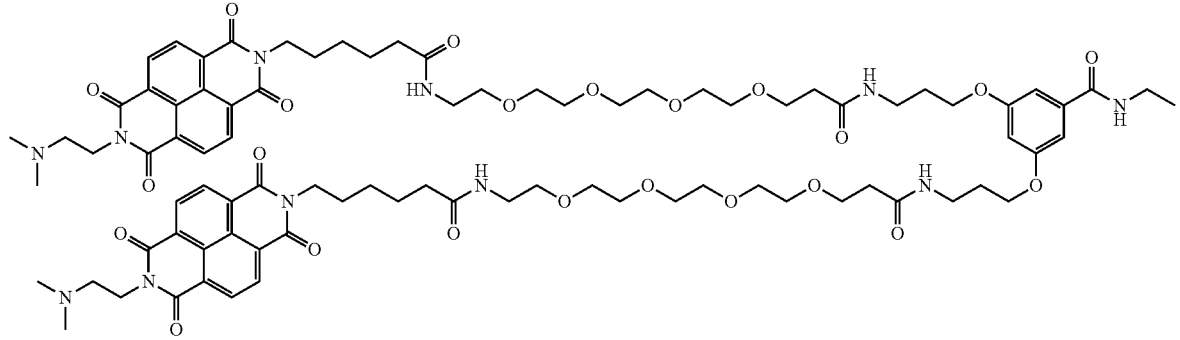

Bis-NDI-C6

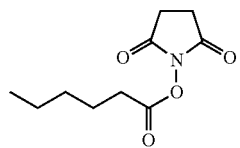

Conjugating a nanocrystal with an emission maximum in the lower wavelength region of the visible spectrum to a DNA-binding molecule affords a photo-stable, nanomaterial-based replacement for common DNA counterstains such as DAPI and Hoechst nucleic acid dyes. The final conjugates can be used to direct and hind the nanomaterial to double-stranded DNA. When a semiconducting nanocrystal is used as the nanomaterial, the photoluminescence of the quantum dot, and possibly of the DNA-binding molecule, will signal the binding of the conjugate to the DNA. If this conjugate is applied to DNA found in the nucleus of a cell, the conjugate will selectively bind to chromatin in the nucleus, providing visualization of the DNA within the nucleus. This provides a fluorescent detection, delineation, and morphology of the nucleus.

Figure 11:
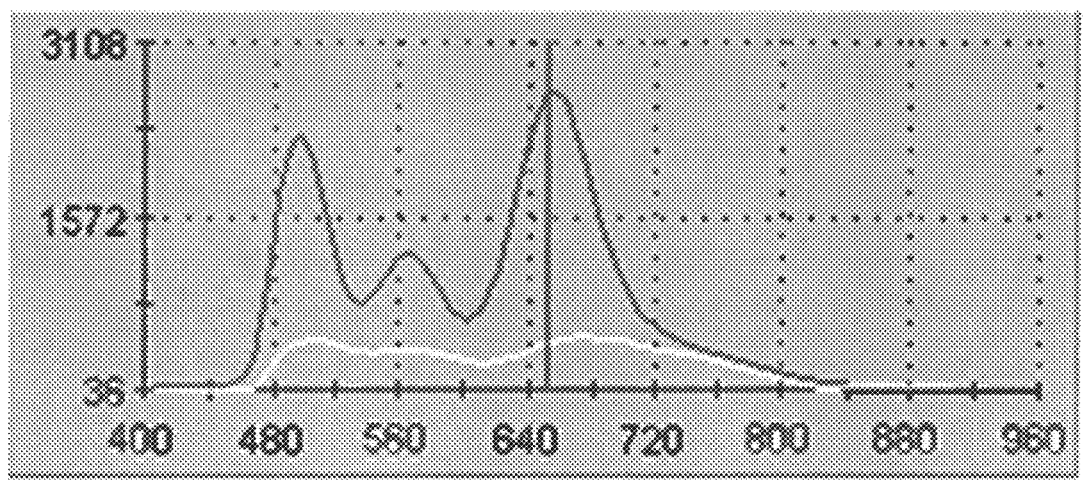
FIG. 11 is a fluorescence spectrum of a mixture of quantum dots that fluoresce at 490 nm, 565 nm, and 655 nm.

Commercially available quantum dots with emission maxima around 490 nm serve as an appropriate nanomaterial that closely matches the spectral maxima of the common DNA dyes. These nanocrystals conjugated to DNA interacting molecules, such as naphthalene diimide derivatives and psoralen, provide a nuclear stain for DNA in tissue that matches and surpasses the performance of the DAPI and Hoechst counterstains. The advantages of the semiconducting nanocrystal system are based upon the photophysical properties of the nanomaterial. For example, the photoluminescence spectrum of a 490-nm quantum dot is narrow and does not significantly overlap with the spectrum of 565-nm quantum dots or any other lower frequency quantum dots (FIG. 11), thereby overcoming the inherent fluorescence spectral overlap of organic DNA dyes. Conversely, longer wavelength-emitting quantum dots in conjunction with DNA binding moieties can be employed to delineate the nucleus in fixed tissue. Thus, quantum dots with photoluminescent properties outside the emission spectra of FISH (fluorescence in situ hybridization) dyes can be utilized without convolution of the FISH signals.

Figure 12:
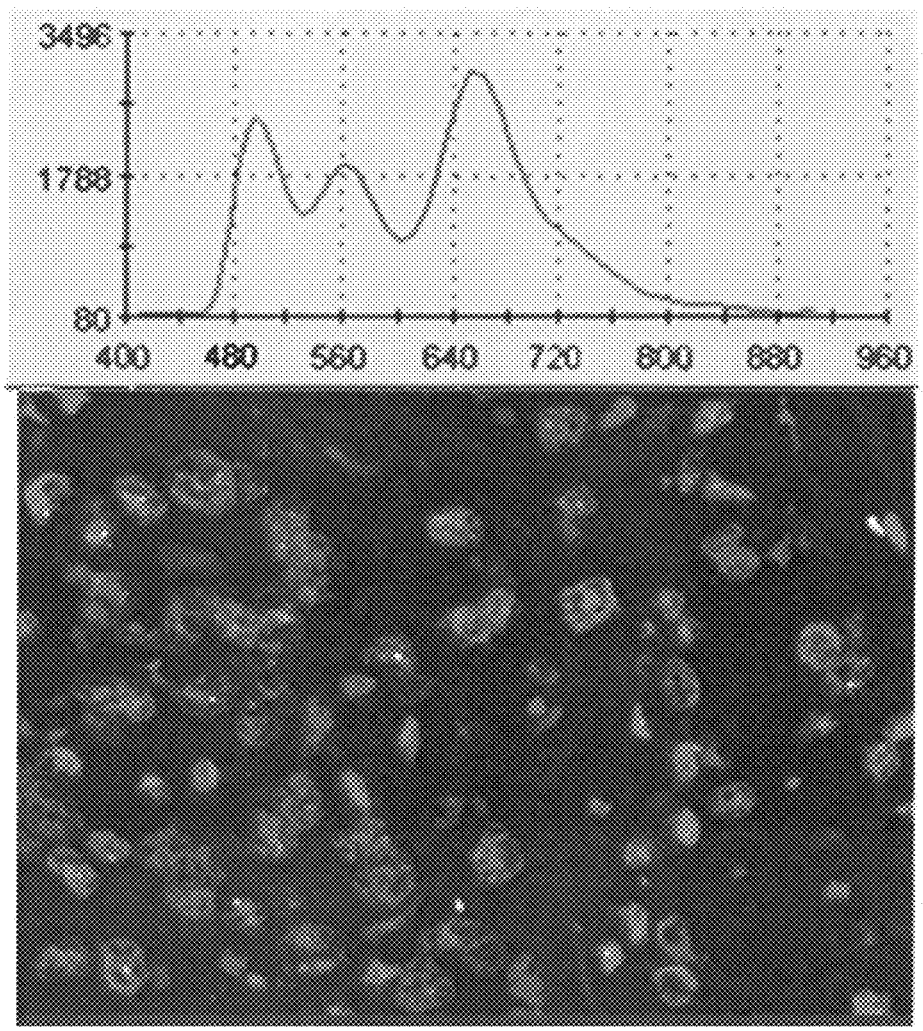
FIG. 12 is a photograph of prostate tissue cells after performing a TMPRSS2 assay. The nuclei are counterstained with a QD490:NDI-C6 conjugate at a concentration of 25 nM. The FISH probes utilizing QD565 and QD655 quantum dots also are clearly visible.
Figure 13:
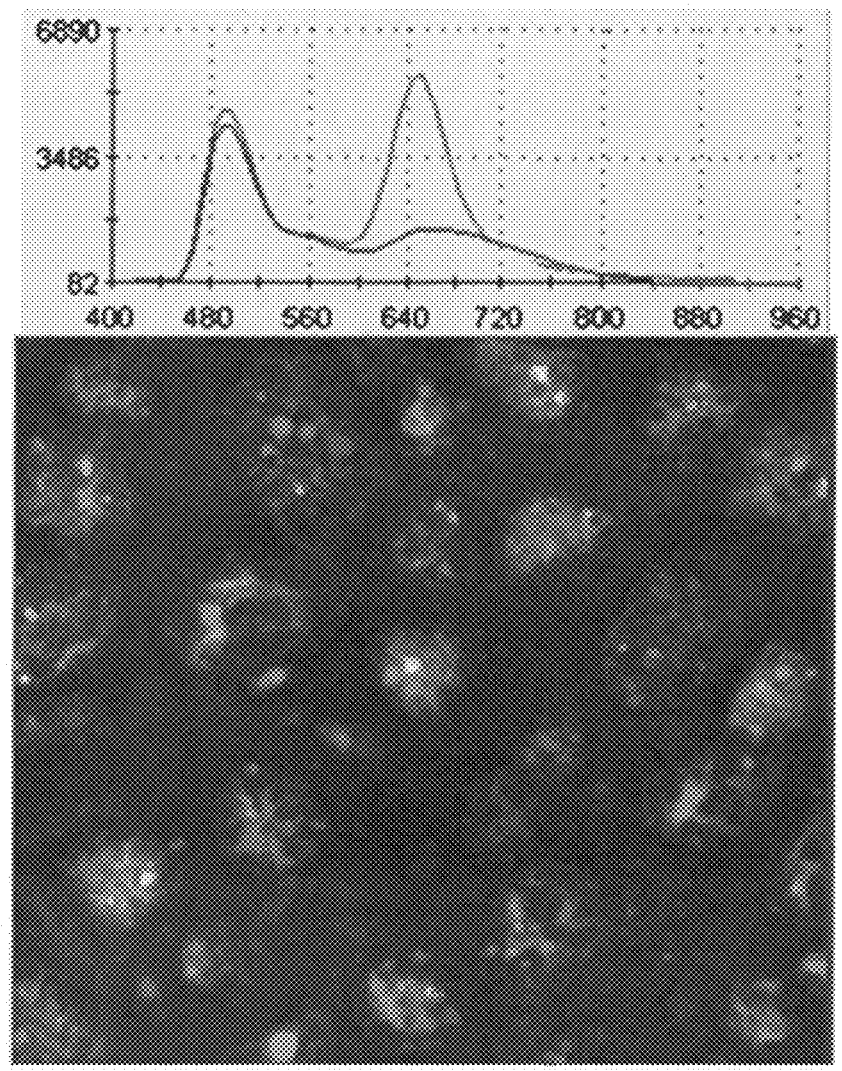
FIG. 13 is a photograph of breast tissue cells after performing an HER2-Chr17 assay. The nuclei are counterstained with a QD490:NDI-C6 conjugate at a concentration of 25 nM. The FISH probes utilizing QD565 and QD655 quantum dots also are clearly visible.

Another advantage is the stability of the photoluminescent signal. Common fluorophores are known to succumb to photobleaching, which results in diminished intensity and changes to spectral signatures in a matter of seconds to minutes. However, in some embodiments, the quantum dot-DNA binding molecule conjugates show no change in the intensity or frequency of the emission under continuous excitation for an excess of 30 minutes. This advantage is fully realized in the conjunction with assays using spectrally complementary quantum dots such as the quantum dot TMPRSS2 prostate assay (FIG. 12). This technology has application to a variety of photoluminescent dark field assays, including the quantum dot-based HER2 gene detection in breast tissue (FIG. 13). The stability of the conjugate signal enables preparation of archivable slides of fixed tissue samples with visualized nuclei, thereby overcoming the intrinsic disadvantage of DAN.

Figure 14:
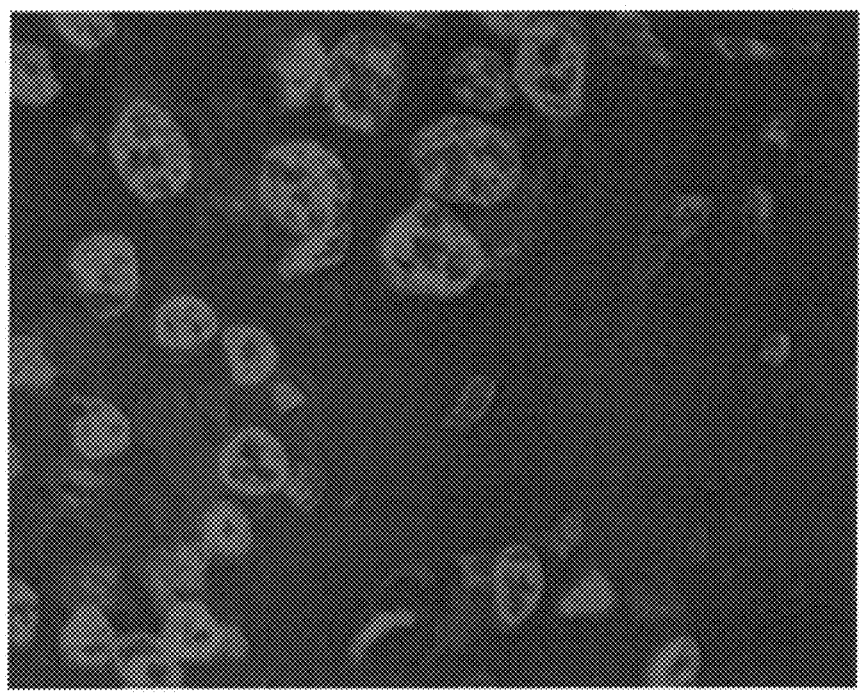
FIG. 14 is a darkfield image of prostate tissue. The nuclei are counterstained with a QD490:NDI-C6 conjugate.
Figure 15:
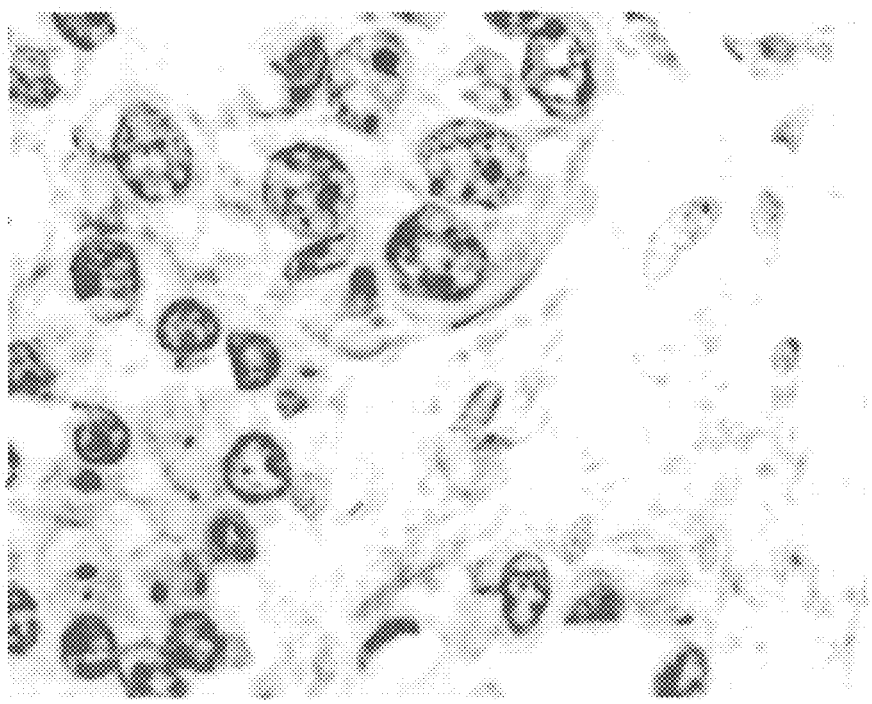
FIG. 15 is a pseudo brightfield hematoxylin and eosin tissue stain produced by converting the darkfield image of FIG. 14. The image has a magnification of 40×.

The quantum dot-based nuclear staining also serves as a fluorescent nuclei marker that can be used in conjunction with the pseudo hematoxylin and eosin imaging techniques. Here the QD490, or any other semiconducting nanocrystal, provides the staining equivalent of hematoxylin. This provides the pseudo brightfield of the dark field images of fluorescent FISH assays (FIGS. 14-15).

V. SAMPLE PREPARATION

The tissue samples described herein can be prepared using any method now known or hereafter developed in the art. Generally, tissue samples are prepared by fixing and embedding the tissue in a medium.

In some examples, an embedding medium is used. An embedding medium is an inert material in which tissues and/or cells are embedded to help preserve them for future analysis. Embedding also enables tissue samples to be sliced into thin sections. Embedding media include, but are not limited to, paraffin, celloidin, OCT™ compound, agar, plastics, or acrylics.

Many embedding media are hydrophobic; therefore, the inert material may need to be removed prior to histological or cytological analysis, which utilizes primarily hydrophilic reagents. The term deparaffinization dewaxing is broadly used herein to refer to the partial or complete removal of any type of embedding medium from a biological sample. In some embodiments, paraffin-embedded tissue sections are dewaxed by using aqueous detergents and heat.

The process of fixing a sample can vary. Fixing a tissue sample preserves cells and tissue constituents in as close to a life-like state as possible and allows them to undergo preparative procedures without significant change. Fixation arrests the autolysis and bacterial decomposition processes that begin upon cell death, and stabilizes the cellular and tissue constituents so that they withstand the subsequent stages of tissue processing, such as for IHC or ISH.

Tissues can be fixed by any suitable process, including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum.

The most commonly used fixative in preparing samples for MC is formaldehyde, generally in the form of a formalin solution (4% formaldehyde in a buffer solution, referred to as 10% buffered formalin). In one example, the fixative is 10% neutral buffered formalin.

In multiple cases, it has been shown that over-fixed tissue (fixed for durations greater than 48 hours) provides a greater amount of background auto-fluorescence than tissue fixed for ~24 hours. The signal intensity of the quantum dot nuclear stain drops significantly (approximately 30-50%) in samples that exceed 48 hours of fixation time, compared to those tissues fixed between 24-48 hours.

Due to the size of a quantum dot conjugate, the nucleus in fixed cells and tissue are not normally accessible. To allow the quantum dot to enter the nucleus and stain the DNA, the tissue must be pretreated with a protease. The duration and concentration of protease treatment, in conjunction with the quantum dot conjugate concentration, determine the degree of the staining of the nucleus. In most tissues, a treatment of 4-8 minutes with the protease (e.g., protease III) is sufficient to allow delineation of the nucleus with the quantum dot counterstain in fixed tissue.

Figure 16:
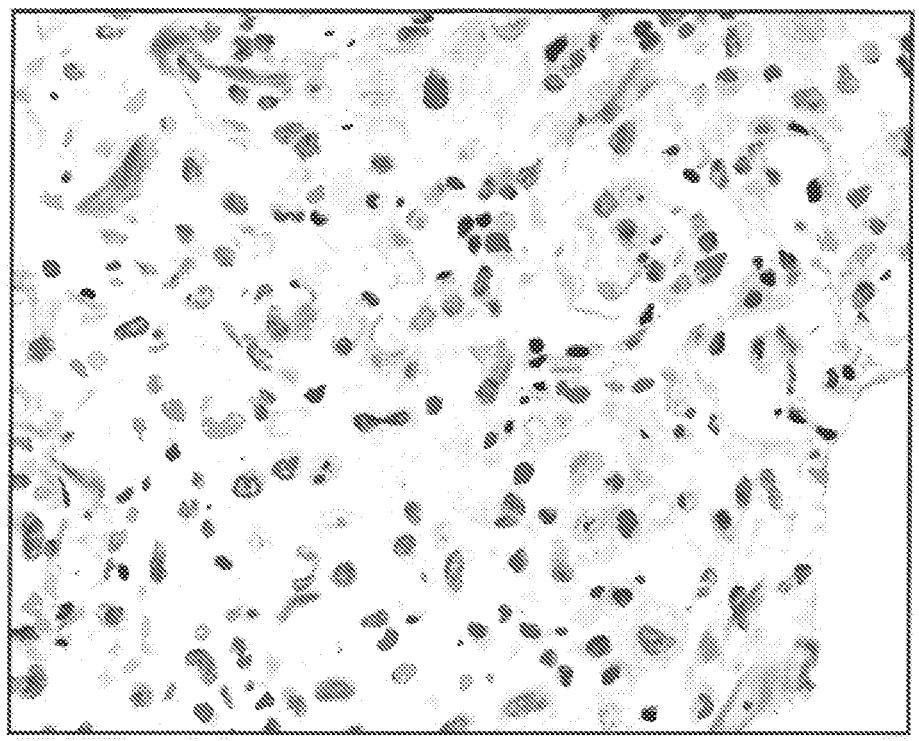
FIG. 16 is a photograph of lung tissue stained with a QD490:NDI-C6 conjugate.
Figure 17:
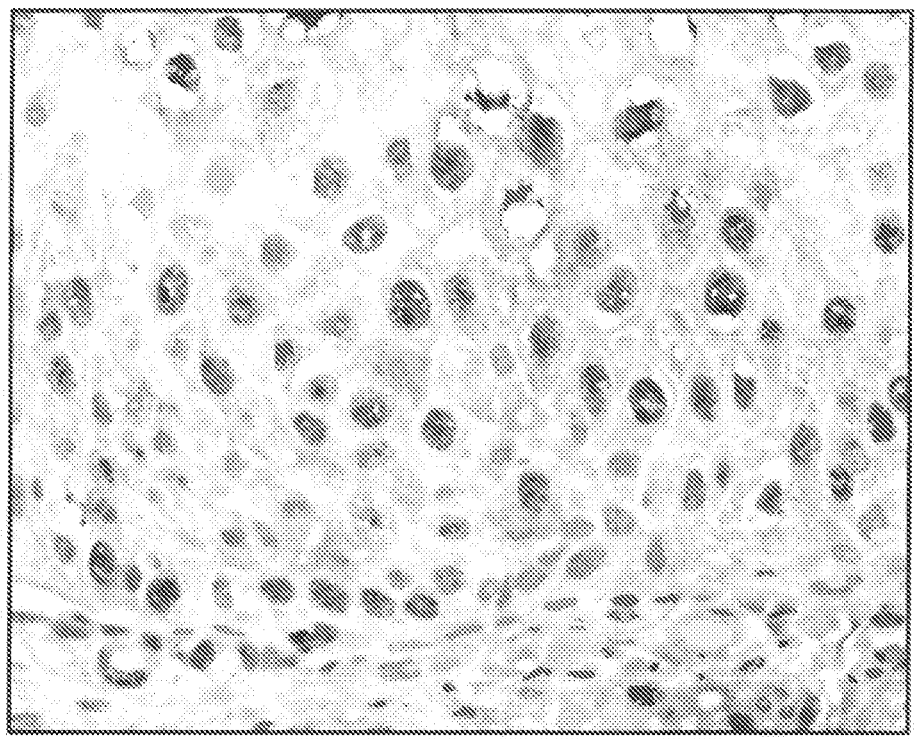
FIG. 17 is a photograph of cervical tissue stained with a QD490:NDI-C6 conjugate.

In addition to tonsil, breast xenografts, and prostate tissue, cervical and lung tissues have been stained with the QD490: NDI-C6 conjugate. Both tissues show excellent staining with minimal amount of background. (FIGS. 16-17.)

VI. TEXTURE MEASUREMENTS

The distribution of the chromosomes or DNA in the nuclei of cells can be qualitatively and/or quantitatively measured using a computer and image analysis techniques. (See, e.g., Rodenacker, et al., *Analytical Cellular Pathology* (2003) 25:1-36.) These measurements, or features, can be used to detect early signs of abnormal cellular behavior and/or diagnose cancer, as well as predict patient outcomes and prognoses.

The features that appear to have the most discriminatory power are texture features. Such features quantitatively describe the intensity variation of the chromatin pattern in the cell nucleus. The most widely used chromatin texture features are based on a statistical or probabilistic assessment of the gray-levels in the rendered microscope image.

Recently a new class of texture features has been introduced based on a structural segmentation of chromatin aggregates (see, e.g., U.S. Pat. No. 7,574,304). In this approach, features are computed for the light and dark particles of a nucleus image. Numerous features can be found in the literature to Characterize the size, shape, boundary and texture of image objects. Although these features were developed for the purpose of characterizing cell nuclei, they can be applied more generally to any image object including segmented nuclear particles.

Some features that may be applied in embodiments of the present disclosure include morphometric features (e.g., area, perimeter, factor), densitometric features (e.g., volume, mean gray value, regional minima dynamics), texture features (e.g., surface area) and contextual features (such as distance to nuclear boundary). With respect to the latter case, contextual features are computed from (i) a neighborhood graph defined on the dark particles; (ii) a neighborhood graph defined on the light particles; and/or (iii) a neighborhood graph defined on both the light and dark particles. The preferred type of neighborhood graph is the Delaunay graph. For a given graph, a co-occurrence matrix can be defined for each particle feature and related neighbors on a digitized two-dimensional space. For example, from the histogram of dark particle areas and the neighborhood graph defined on these particles, it is possible to construct a matrix such that the entry in the i-th row and the j-th column represents the number of times a particle of area i is adjacent to a particle of area j. To keep the matrix size manageable and/or to avoid having a sparse matrix, the number of bins in the histogram of the feature under consideration can be reduced. For each co-occurrence matrix, co-occurrence matrix features can be computed and used as nucleus features. Once all such features have been computed, standard pattern recognition algorithms are used for feature selection and classifier training. Algorithms such as discriminate analysis, artificial neural networks and/or support vector machines may be applied to the problem in a standardized test/train/validation routine well known to those skilled in the art. The result of such classifier design is generally a receiver operating characteristic (ROC) curve that summarizes the sensitivity and specificity trade-offs available to the system. One advantage of the present disclosure over the prior art is that the feature measurements that are input to such pattern recognition systems are of far higher quality than previously possible with lower contrast and less specific nuclear counterstains. This translates into more accurate measurements, better ROC sensitivity and specificity, and hence more powerful diagnostic, predictive and/or prognostic tests.

VII. KITS

Embodiments of a kit for performing nucleus visualization include a nanomaterial/DNA-binding moiety conjugate and a reaction buffer having a salt concentration and pH sufficient to enable the conjugate to enter a nucleus within a tissue sample that has been pretreated with a protease enzyme composition. In some embodiments, the nanomaterial is a nanoparticle, such as a metal nanoparticle or a quantum dot. The DNA-binding molecule may be a minor groove binder, a major groove binder, an intercalator, a DNA alkylating agent, or a combination thereof.

In some embodiments, the kits further include a protease enzyme and a protease buffer having a salt concentration and pH sufficient to allow the protease enzyme to exhibit proteolytic activity. The protease enzyme and protease buffer may be combined and provided as a protease composition. The kits also typically include an instruction sheet for performing the nucleus visualization method.

VIII. EXAMPLES

Example 1

NDI-C6-NHS Synthesis

Scheme 1:

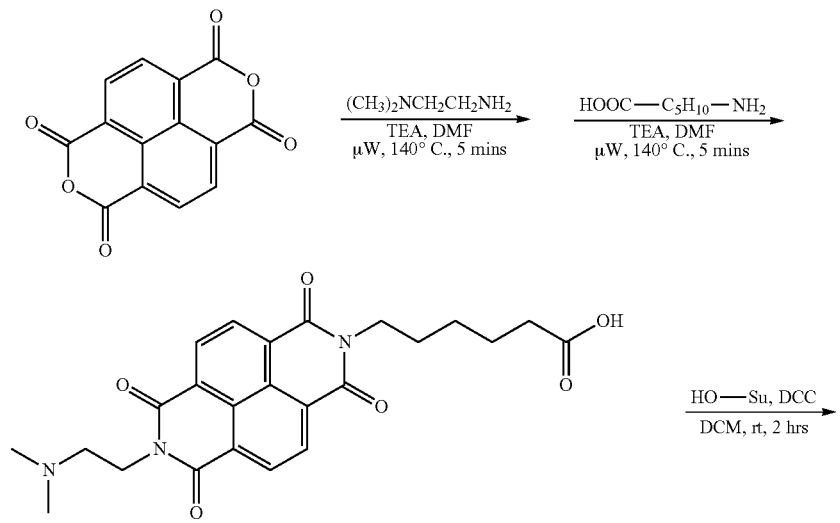

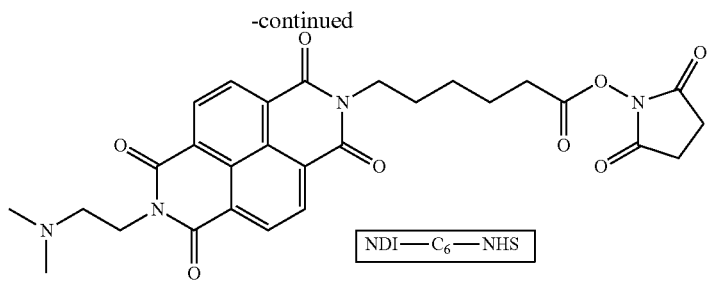

2

Compound (1)

In a 10 mL CEM microwave reaction vessel with a stir bar 1,4,5,8-naphthalenetetracarboxylic dianhydride 50 mg (0.186 mmol, 1 equivalent, Sigma N818), N,N-dimethylethylenediamine 20.3 µL (0.186 mmol, 1 equivalent, Sigma 39030) and triethylamine 25 µL (0.186 mmol, 1 equivalent, Sigma T0886) were dissolved in anhydrous DMF 3 mL (EMD biosciences). The mixture was heated to 140° C., with cooling during irradiation to maintain a temperature of 140° C., in a CEM Discover microwave for five minutes, 6-Aminocaproic acid 24 mg (0.186 mmol, 1 equivalent, Sigma A2504) and triethylamine 50 µL (0.372 mmol, 2 equivalents, Sigma T0886) were added to the reaction and heated to 140° C., with cooling for a further five Minutes. The crude reaction was purified by preparative reverse phase HPLC (10:90 $CH_3CN$:0.05% TFA in $H_2O$ gradient to 90:10 over 60 minutes, monitoring at 360 nm). A brown powder was isolated in 63% yield. Analytical HPLC retention time 5.06 mins. $^1$H NMR (400 MHz, $d_6$-DMSO) δ 9.54 (s, 1H), 8.69 (s, 4H), 4.43 (t, J=5.6 Hz, 2H), 4.06 (t, J=7.4 Hz, 2H), 3.49 (t, J=5.5 Hz, 3H), 2.92 (s, 6H), 2.24 (t, J=7.3 Hz, 2H), 1.75-1.63 (m, 2H), 1.63-1.51 (m, 2H), 1.39 (dd, J=15.0, 8.0 Hz, 2H). $^{13}$C NMR (101 MHz, DMSO) δ 174.89, 163.65, 163.06, 130.98, 130.90, 126.95, 126.74, 126.66, 126.58, 55.14, 43.21, 35.90, 33.94, 27.61, 26.48, 24.67. MS (TOF ESI+) m/z 452.1 (M+H).

Compound (2)

(1) 44 mg (0.097 mmol, 1 equivalent), N-hydroxysuccinimide 12.3 mg (0.107 mmol, 1.1 equivalents, Sigma 130672), triethylamine 68 µL (0.485 mmol, 5 equivalents, Sigma T0866) and N,N'-dicyclohexylcarbodiimide 107 µL (1.0 M solution in dichloromethane, 0.107 mmol, 1.1 equivalents, Sigma 379115) were dissolved in 2 dichloromethane (Sigma). The reaction was stirred for 2 hours, filtered through a sintered glass funnel and concentrated in vacuo. The residue was dissolved in 25 mL of ethyl acetate, washed with two portions of deionized water, dried over anhydrous sodium sulfate, filtered and concentrated to a brown oil, yield 90%. Analytical HPLC retention time 6.65 mins. $^1$H NMR (400 MHz, $CDCl_3$) δ 8.77 (s, 4H), 4.38 (t, J=6.7 Hz, 2H), 4.29-4.16 (m, 2H), 2.83 (s, 4H), 2.74 (t, J=6.5 Hz, 2H), 2.66 (t, J=7.4 Hz, 2H), 2.39 (s, 6H), 1.84 (tt, J=15.4, 7.7 Hz, 4H), 1.57 (dd, J=15.0, 7.2 Hz, 2H). $^{13}$C NMR (101 MHz, $CDCl_3$) δ 169.14, 168.46, 162.99, 162.84, 131.02, 130.98, 126.78, 126.71, 126.62, 56.86, 45.68, 40.49, 38.47, 30.78, 27.52, 26.14, 25.58, 24.23, MS (TOF ESE+) 549.1 (M+H).

Example 2

NDI-PEG$_4$-NHS Synthesis

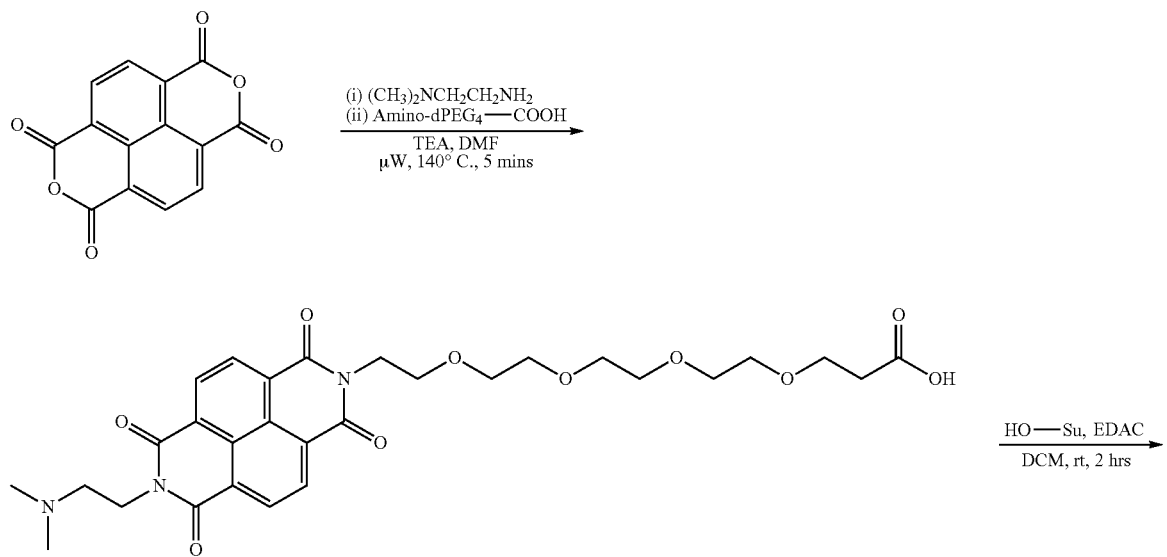

3

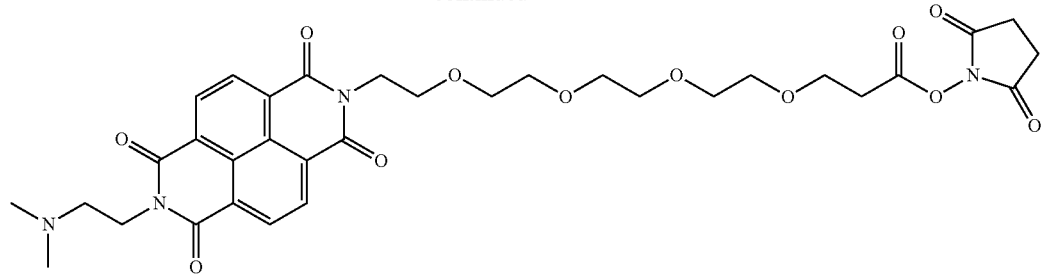

4

Compound (3)

In a 10 mL CEM microwave reaction vessel with a stir bar 1,4,5,8-naphthalenetetracarboxylic dianhydride 50 mg (0.186 mmol, 1 equivalent, Sigma N818), N,N-dimethylethylenediamine 20.3 μL (0.186 mmol, 1 equivalent, Sigma 39030) and triethylamine 25 μL (0.186 mmol, 1 equivalent, Sigma T0886) were dissolved in anhydrous N,N-dimethylformamide 3 mL (EMD biosciences). The mixture was heated to 140° C. in a CEM Discover microwave, with cooling, for five minutes. Amino-dPEG$_4$-COOH 49.4 mg (0.186 mmol, 1 equivalent, QuantaBioDesign 10244) and triethylamine 50 μL (0.372 mmol, 2 equivalents, Sigma T0886) were added to the reaction and heated to 140° C., with cooling, for a further five minutes. The crude reaction was purified by preparative reverse phase HPLC (10:90 CH$_3$CN:0.05% TFA in H$_2$O gradient to 90:10 over 60 minutes, monitoring at 360 nm). A brown oil was isolated in 63% yield. Analytical HPLC retention time 5.69 mins. MS (TOF ESI+) m/z 586.2 (M+H).

Compound (4)

(3) 69 mg (0.118 mmol, 1 equivalent), N-hydroxysuccinimide 14.2 mg (0.124 mmol, 1.05 equivalents, Sigma 130672) and N-(3-Dimethylaminopropyl)-N'-ethylcarbodiimide hydrochloride 24.8 mg (0.130 mmol, 1.1 equivalents, Sigma 379115) were dissolved in 2 mL of dichloromethane (Sigma). The reaction was stirred overnight and concentrated in vacuo. The residue was dissolved in 25 mL of ethyl acetate, washed with two portions of deionized water and concentrated. A brown oil was isolated in quantitative yield. Analytical HPLC retention time 6.03 mins. MS (TOF ESI+) 683.1 (M+H).

Example 3

(NMe$_3$)$^+$-NDI-C6-NHS Synthesis

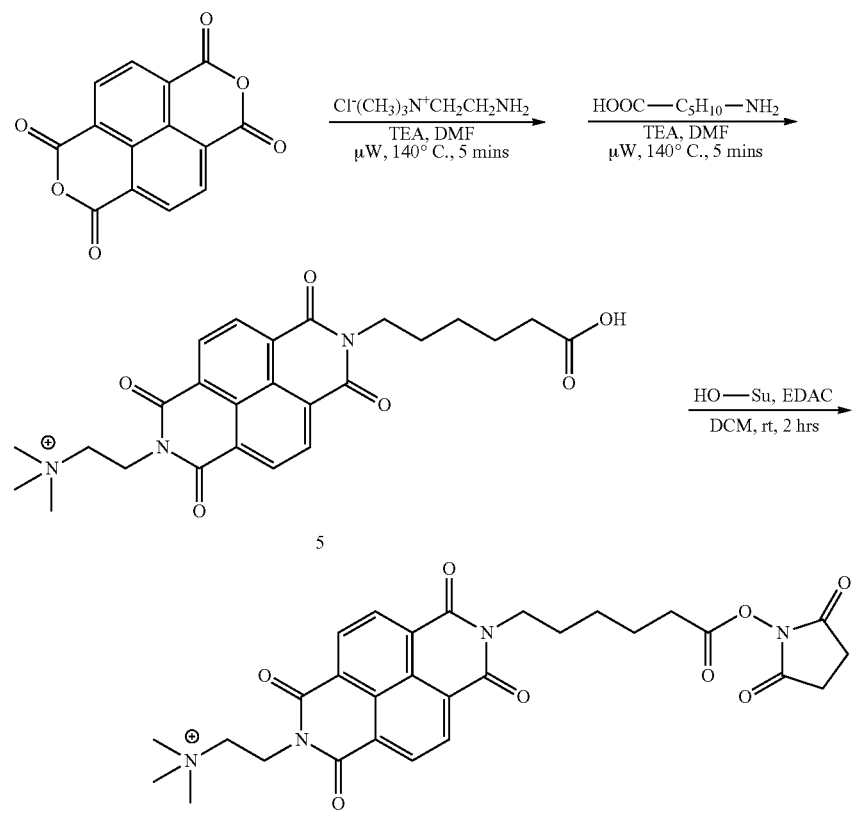

Compound (5)

In a 10 mL CEM microwave reaction vessel with a stir bar 1,4,5,8-naphthalenetetracarboxylic dianhydride 50 mg (0.186 mmol, 1 equivalent, Sigma N818), (2-aminoethyl)trimethylammonium chloride hydrochloride 32.6 mg (0.186 mmol, 1 equivalent, Sigma 284556) and triethylamine 78 µL (0.558 mmol, 3 equivalents, Sigma 10886) were dissolved in anhydrous DMF 3 mL (EMD biosciences)). The mixture was heated to 140° C. in a CEM Discover microwave, with cooling, for five minutes. 6-Aminocaproic acid 24 mg (0.186 mmol, 1 equivalent, Sigma A2504) and triethylamine 78 µL (0.558 mmol, 3 equivalents, Sigma T0886) were added to the reaction and heated to 140° C., with cooling, for a further five minutes. The crude reaction was purified by preparative reverse phase HPLC (10:90 $CH_3CN$:0.05% TFA in $H_2O$ gradient to 90:10 over 60 minutes, monitoring at 360 nm). A green/brown oily solid was isolated in 91% yield. HPLC retention time 6.09 mins.

Compound (6)

(5) 79 mg (0.169 mmol, 1 equivalent), N-Hydroxysuccinimide 23.4 mg (0.203 mmol, 1.2 equivalents, Sigma 130672), triethylamine 70.8 µL (0.508 mmol, 3 equivalents, Sigma 10866) and N-(3-dimethylaminopropyl)-N'-ethylcarbodiimide hydrochloride 38.9 mg (0.203 mmol, 1.2 equivalents, Sigma 379115) were dissolved in 2 mL dichloromethane (Sigma). The reaction was stirred overnight and concentrated in vacuo. The residue was dissolved in 25 mL of ethyl acetate, washed with deionized water (2×25 mL). The aqueous layer was extracted with 25 mL of dichloromethane. The organic layers were combined and concentrated. A brown oil was isolated in quantitative yield. Analytical HPLC retention time 6.94 mins.

Example 4

Synthesis of Bis Linker Containing NDI-C6

Scheme 4:

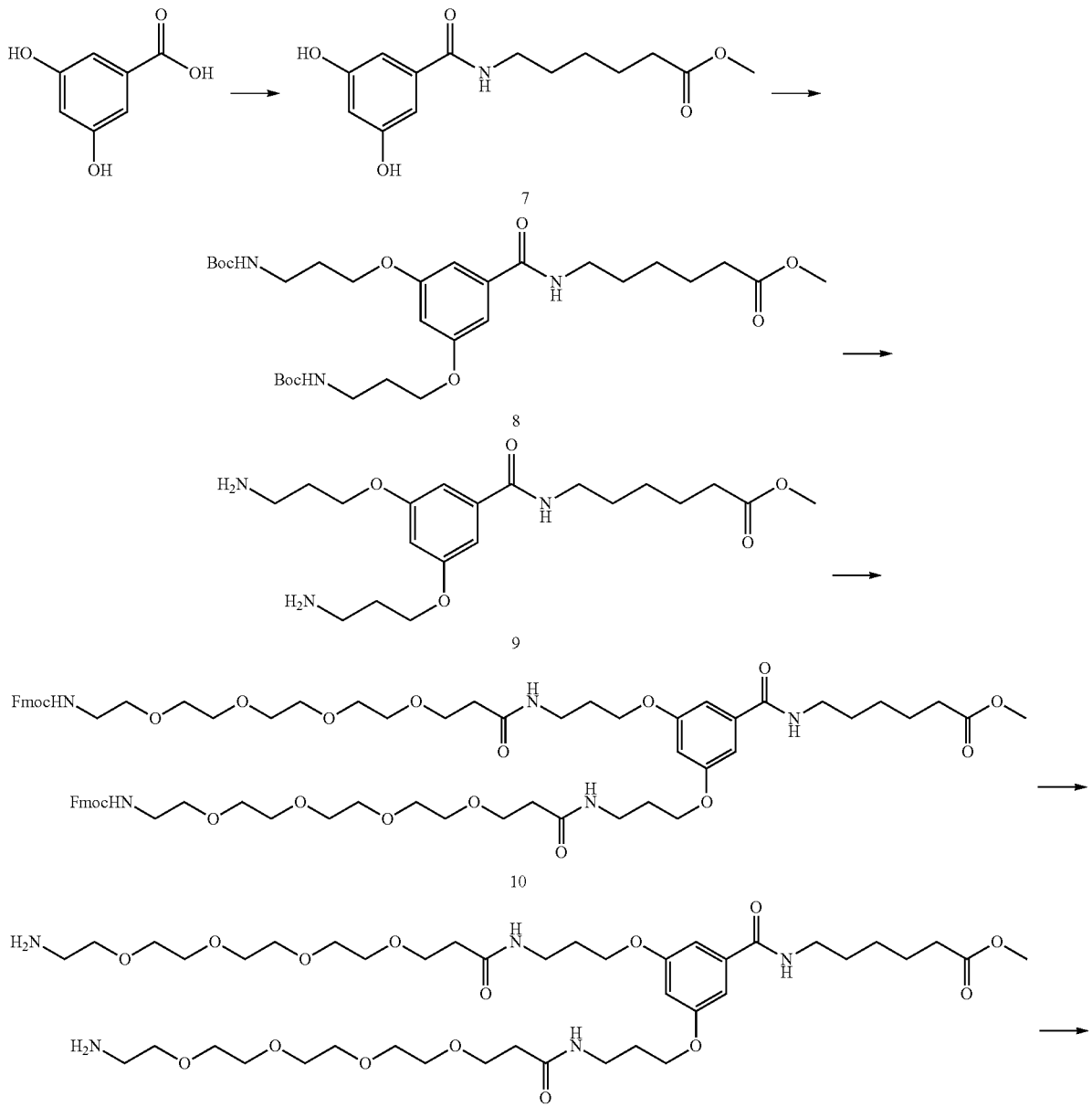

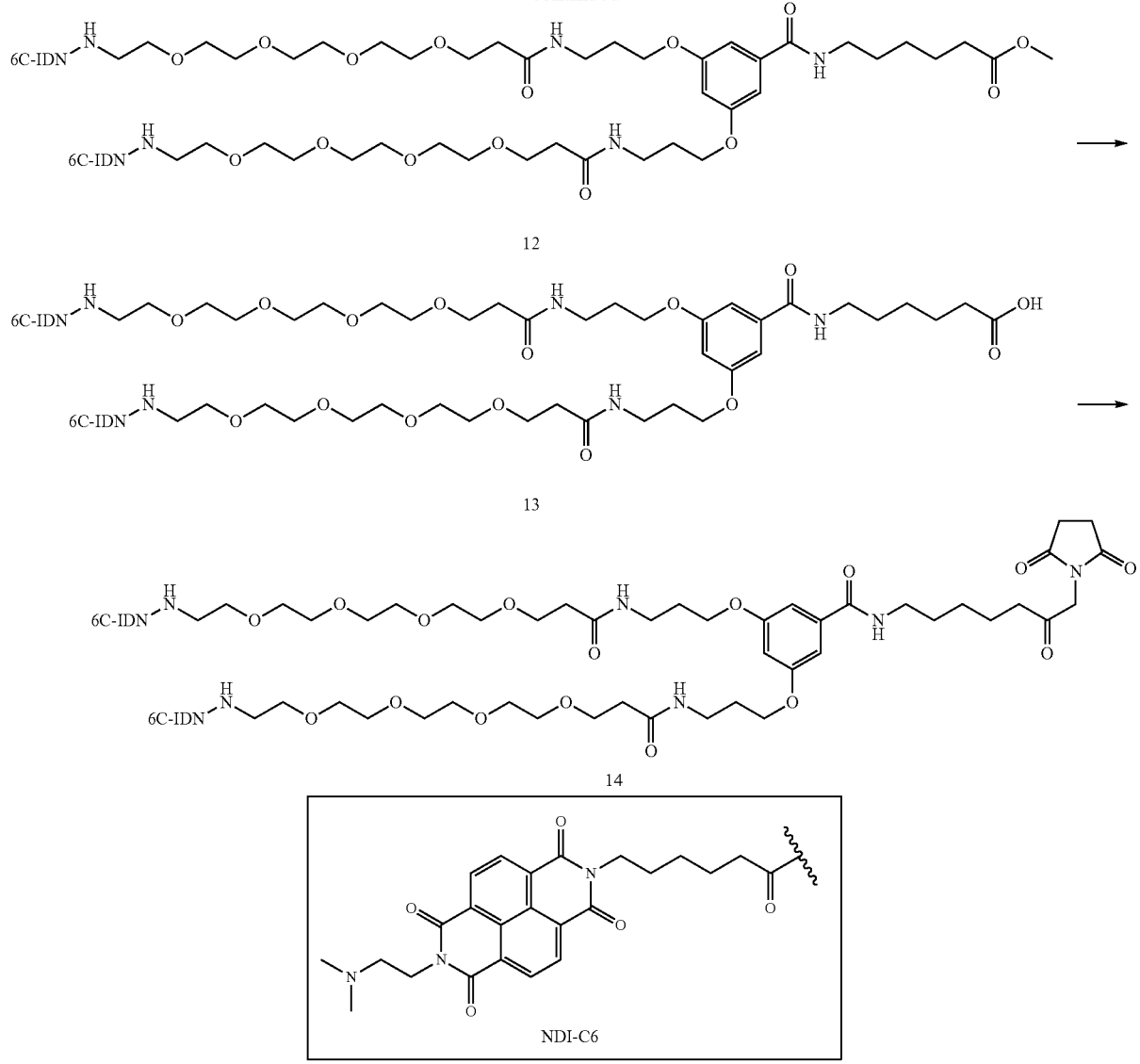

Compound (7)

3,5-dihydroxybenzoic acid 3 g (19.5 mmol, 1 equivalent, TCI D2554), methyl aminohexanoate 3.89 g (21.4 mmol, 1.1 equivalents, Fluka 07270), triethylamine 8.14 mL (584 mmol, 3.0 equivalents, Sigma T0886) and N,N'-dicyclohexylcabodiimide 29.2 mL (1.0 M solution, 29.2 mmol, 1.5 equivalents, Sigma 379115) were diluted with 100 mL of dichloromethane stirred overnight. The crude reaction was filtered and concentrated in vacuo. The residue was diluted in ethyl acetate (200 mL) and washed with 1 M HCl (200 mL), saturated NaHCO$_3$ (200 mL) and brine (200 mL). The solution was concentrated in vacuo, passed through a 0.2 μm syringe filter and purified by flash chromatography on a 330 g Redisep® (Teledyne Isco, Inc., Lincoln, Neb.) silica gel column (ethyl acetate:hexanes 5:95 gradient to 100:0). Yield 23% of a white powder. Analytical HPLC retention time 4.08 mins. $^1$H NMR (400 MHz, MeOD) δ 6.71 (d, J=2.2 Hz, 2H), 6.42 (t, J=2.2 Hz, 1H), 4.92 (s, 3H), 3.66 (s, 3H), 3.41-3.29 (m, 3H), 2.35 (t, J=7.4 Hz, 2H), 1.64 (ddt, J=18.4, 14.9, 7.4 Hz, 4H), 1.47-1.33 (m, 2H). $^{13}$C NMR (101 MHz, MeOD) δ 174.53, 169.19, 158.43, 136.67, 105.29, 105.05, 50.61, 39.31, 33.28, 28.71, 26.09, 24.29. MS (TOF ESI+) 282.4 (M+H).

Compound (8)

(7) 695 mg (2.47 mmol, 1 equivalent), tert-butyl 3-bromopropylcarbamate 1.765 g (7.41 mmol, 3 equivalents) and potassium carbonate 1.366 g (9.88 mmol, 4 equivalents, Sigma 310263) were diluted with 12 mL of N,N-dimethylformamide and heated to 50° C. overnight. The solvent was removed in vacuo, the residue was dissolved with ethyl acetate, washed with brine, dried over anhydrous magnesium sulfate, filtered and concentrated to a white solid. The crude material was purified by flash chromatography (50 g Biotage® SNAP column (Biotage, LLC, Charlotte, N.C.), ethyl acetate:hexanes 12:88 gradient to 100:0). Yield 73% of a white solid. Analytical HPLC retention time 10.34 mins. $^1$H NMR (400 MHz, CDCl$_3$) δ 6.89 (d, J=2.2 Hz, 2H), 6.53 (t, J=2.2 Hz, 1H), 6.49 (t, J=5.7 Hz, 1H), 4.84 (s, 2H), 4.01 (t, J=5.9 Hz, 4H), 3.66 (s, 3H), 3.44 (dd, J=13.1, 6.9 Hz, 2H), 3.31 (dd, J=12.3, 6.1 Hz, 4H), 2.33 (t, J=7.4 Hz, 2H), 1.96 (p, J=6.1 Hz, 4H), 1.65 (tt, J=15.2, 7.5 Hz, 4H), 1.51-1.35 (m, 20H). $^{13}$C NMR (101 MHz, CDCl$_3$) δ 174.12, 167.24, 159.95, 156.03, 136.95, 105.61, 104.28, 79.26, 65.86, 51.55, 39.78, 37.78, 33.84, 29.47, 29.21, 28.41, 26.39, 24.44. MS (TOF ESI+) 596.8 (M+H).

Compound (9)

(8) 587 mg (0.99 mmol, 1 equivalent) was dissolved in 5 mL of a 20% solution of trifluoroacetic acid in dichloromethane and stirred at room temperature for 2.5 hours. The solvent was removed in vacuo and the residue azeotroped with toluene/methanol. The material was carried forward without any further purification. Analytical HPLC retention time 4.77 mins. $^1$H NMR (400 MHz, D$_2$O) δ 6.77 (s, 2H), 6.59 (s, 1H), 4.02 (t, J=5.7 Hz, 4H), 3.22-3.14 (m, 5H), 3.08 (t, J=7.1 Hz, 4H), 2.20 (t, J=6.6 Hz, 2H), 2.02 (dt, J=12.7, 6.4 Hz, 4H), 1.44 (d, J=2.6 Hz, 4H), 1.19 (dd, J=14.6, 7.4 Hz, 2H). $^{13}$C NMR (101 MHz, D$_2$O) δ 178.76, 177.34, 169.73, 169.71, 162.89, 162.54, 159.24, 136.18, 117.65, 114.75, 106.06, 104.75, 65.79, 51.93, 48.77, 39.69, 37.32, 33.55, 33.42, 27.92, 27.87, 26.30, 25.52, 25.47 23.83. MS (TOF ESI+) 418.5 (M+Na).

Compound (10)

(9) 660.4 mg (1.06 mmol, 1 equivalent), Fmoc-dPEG$_4$-NHS 1.548 g (2.65 mmol, 2.5 equivalents) and diisopropylethylamine 553 µL (3.18 mmol, 3 equivalents, Fluka 03440) were dissolved in 5.3 mL of dichloromethane and stirred at room temperature overnight. The crude reaction was purified by flash chromatography (Biotage SNAP 50 g silica gel column, 100:0 ethyl acetate:methanol gradient to 85:15). Isolated 577 mg of a pale brown oil 41%. Analytical HPLC retention time 10.51 mins. $^1$H NMR (400 MHz, CDCl$_3$) δ 7.75 (d, J=6.7 Hz, 2H), 7.60 (d, 6.2 Hz, 2H), 7.50-7.35 (m, 3H), 7.30 (d, J=6.4 Hz, 2H), 6.97 (s, 1H), 6.50 (s, 1H), 4.32 (d, J=5.8 Hz, 2H), 4.21 (d, J=5.4 Hz, 1H), 3.98 (s, 2H), 3.62 (d, J=19.2 Hz, 20H), 3.42 (dd, J=31.9, 4.0 Hz, 11H), 3.12 (s, 2H), 2.53 (d, J=23.4 Hz, 4H), 2.29 (s, 1H), 1.94 (s, 2H), 1.62 (d, J=6.6 Hz, 3H), 1.41 (dd, J=17.6, 5.6 Hz, 11H). $^{13}$C NMR (101 MHz, CDCl$_3$) δ 174.20, 167.34, 161.85, 161.51, 159.91, 157.34, 143.93, 141.22, 136.80, 127.70, 127.08, 125.16, 119.94, 115.39, 105.82, 70.05, 69.80, 67.55, 66.79, 65.90, 53.62, 51.50, 50.62, 47.12, 41.98, 40.61, 39.90, 36.60, 33.88, 29.13, 28.74, 26.47, 25.28, 24.54, 18.53, 17.40, 11.80. MS (TOF ESI+) 1334.8 (M+H).

Compound (11)

Figure 18:
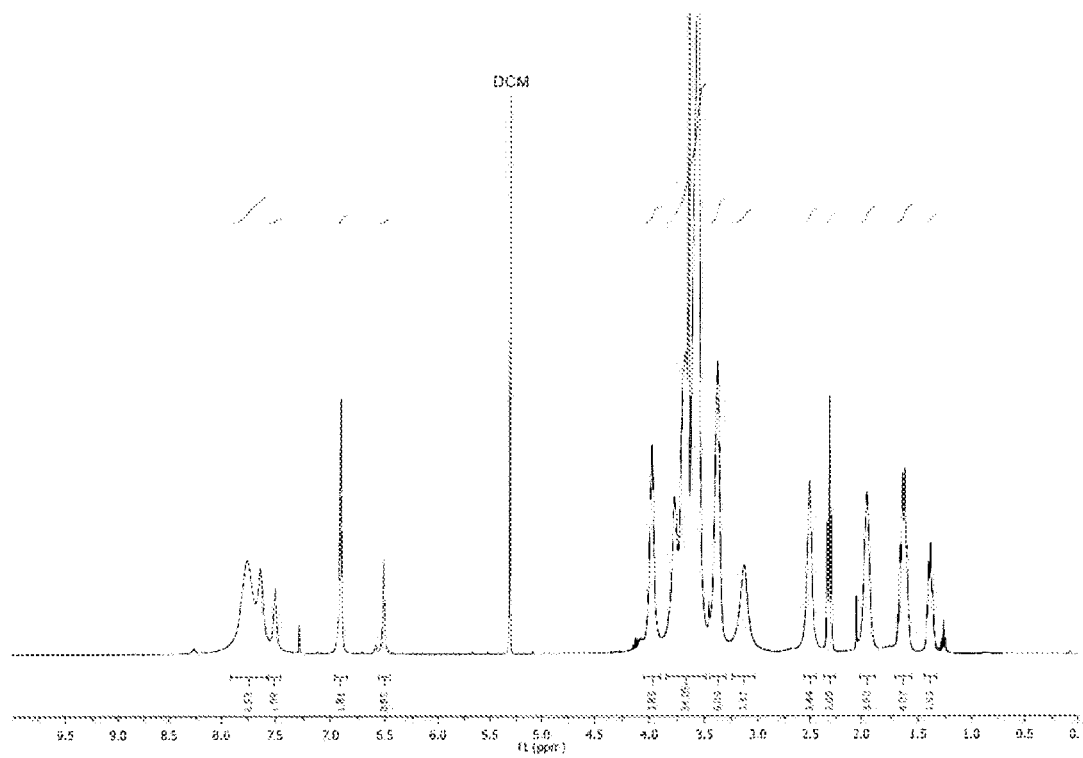
FIG. 18 is the $^1$H NMR spectrum of compound (11), Scheme 4.
Figure 19:
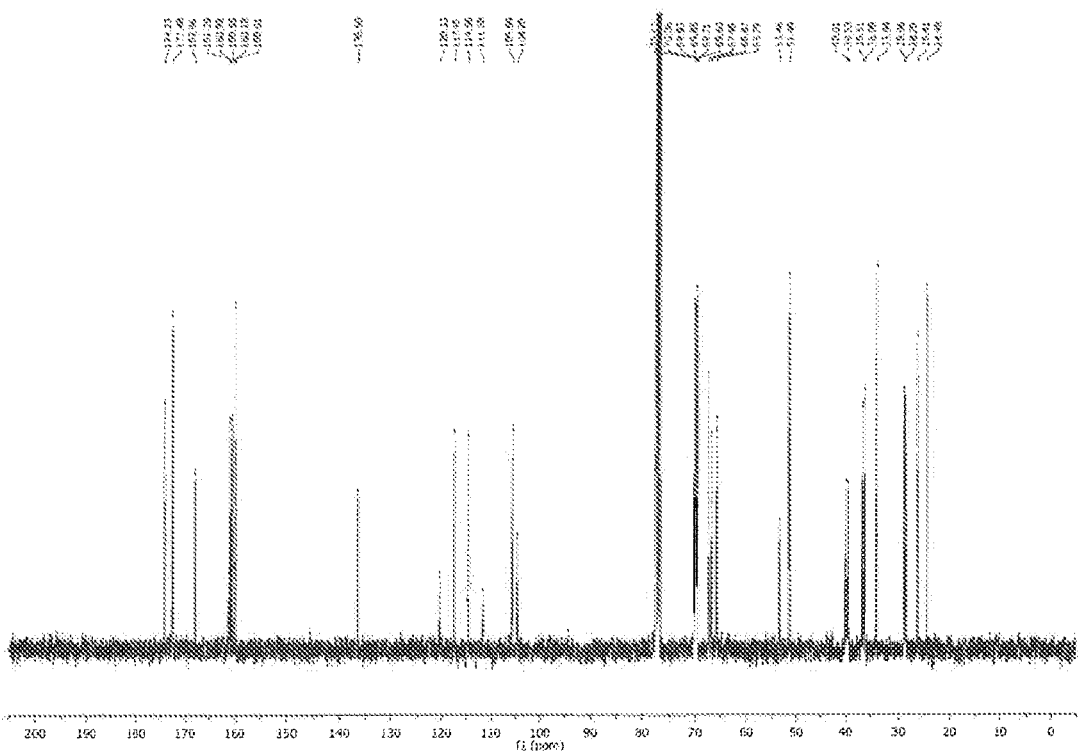
FIG. 19 is the $^{13}$C NMR spectrum of compound (11), Scheme 4.

(10) 577 mg (0.432 mmol, 1 equivalent) and 135 µL (0.9 mmol, 2.1 equivalents) were dissolved in 2 mL of N,N-dimethylformamide and stirred overnight. The solvent was removed in vacuo. The residue was dissolved in water (50 mL) and washed with dichoromethane (50 mL) and ethyl acetate (50 mL). The crude material was purified by preparative reverse phase HPLC (10:90 CH$_3$CN:0.05% TFA in H$_2$O gradient to 90:10 over 60 minutes). Isolated yield 23.4%. Anal HPLC retention time 5.37 mins. MS (TOF ESI+) 890.6 (M+H). FIGS. 18 and 19 depict the $^1$H and $^{13}$C NMR spectra of compound (11), respectively.

Compound (12)

(11) 89.9 mg (0.08 mmol, 1 equivalent), (2) 110.3 mg (0.201 mmol, 2.5 equivalents) and diisopropylethylamine 42 µL (0.241 mmol, 3 equivalents) were dissolved in 3 mL of dichloromethane and stirred overnight at room temperature. The crude material was purified by preparative HPLC (30:70 CH$_3$CN 0.05% TFA isocratic). $^1$H NMR (400 MHz, CDCl$_3$) δ 7.70 (d, J=48.5 Hz, 1H), 7.50 (s, 1H), 6.91 (s, 2H), 6.51 (s, 1H), 3.98 (s, 4H), 3.85-3.49 (m, 34H), 3.38 (s, 6H), 3.13 (s, 3H), 2.51 (s, 3H), 2.32 (t, J=7.4 Hz, 2H), 1.95 (s, 4H), 1.71-1.56 (m, 4H), 1.44-1.33 (m, 2H). $^{13}$C NMR (101 MHz, CDCl$_3$) δ 174.23, 172.48, 167.96, 161.29, 160.92, 160.55, 160.18, 160.01, 136.50, 120.33, 117.45, 114.56, 111.68, 105.69, 104.70, 70.12, 70.06, 69.93, 69.85, 69.71, 69.60, 67.46, 66.82, 65.79, 53.46, 51.49, 40.01, 39.53, 36.51, 36.08, 33.84, 28.96, 28.70, 26.41, 24.48. MS (TOF ESI+) 1756.9 (M+H).

Compound 13 can be synthesized by hydrolyzing the methyl ester of Compound 12 under alkaline conditions using well-established methods, e.g., lithium hydroxide. Compound 13 can be converted to Compound 14 using the same conditions and reagents used to synthesize Compounds 2, 4 and 6.

Example 5

Evaluation of HER2 DNA Probe and Chromosome 17 Probe on HER2 3-in-1 Xenografts Using QD490:NDI-C6

Staining Protocol:

Although the DNA staining protocol presented below refers to HER2 DNA (Ventana Medical Systems, Inc. (VMSI) Cat. No. 780-4332) and/or Chromosome 17 (VMSI Cat. No. 780-4331) probes on HER2 3-in-1 xenografts (VMSI Cat. No. 783-4332) in conjunction with QD490:NDI-C6, it can be generalized to include all gene probe assays. The protocol can be varied as needed, depending upon the gene probe and tissue type. The following is the adapted procedure from the automated VMSI Benchmark® XT Instrument:

1. The formalin-fixed paraffin embedded tissue on the slide was heated to 75° C. for 4 minutes and treated twice with EZPrep™ (10×, VMSI #950-102), volume adjusted at 75° C. before application of Liquid Coverslip™ (VMSI #650-010). Then slide was heated to 76° C. for 4 minutes, the slide was rinsed and EZPrep™ volume adjusted, followed with Liquid Coverslip™ to deparaffinize the tissue. The slide was cooled to 37° C., incubated for 4 minutes and rinsed once with Reaction Buffer (10×, VMSI #950-300).
2. The slide then was heated to 95° C. and pretreated with Cell Condition #2 (CC2 VMSI #950-123) for three cycles of 8, 12, and 8 minutes followed by a short application of the Liquid Coverslip™ after each cycle. Then slide heater was disabled, and the slide was rinsed three times with reaction buffer followed by an application of Liquid Coverslip™ each time.
3. The slide was heated to 37° C., incubated for 4 minutes and rinsed once with reaction buffer. ISH-Protease 3 was applied for 8 minutes and rinsed twice with reaction buffer.
4. The slide was rinsed twice with SSC (10×, VMSI #950-110).
5. One drop of silver in situ hybridization (SISH) detection solution (a component of the VMSI SISH Detection Kit #780-001) was applied, and incubated for 4 minutes.
6. Two drops DNP-labeled HER2 DNA probe (VMSI #780-4332) or DNP-labeled Chromosome 17 Probe (VMSI #780-4331) were applied and incubated for 4 minutes, and the slide then was heated to 95° C. for 12 minutes for nucleic acid denaturation. (DNP=2,4-dinitrophenol.)
7. After the 12 minute incubation, short Liquid Coverslip™ was applied, and the slide was hybridized at 52° C. for 2 hours when using HER2 DNA probe, or at 44° C. for 2 hours when using Chromosome 17 probe.
8. After the hybridization of the probe, the slide was rinsed in SSC twice and underwent three stringency washes of 2.0×SSC at 72° C. for 8 minutes each, after which the slide was allowed to cool.

9. The slide was rinsed in reaction buffer and warmed up to 37° C. for 4 minutes. Then, one drop of QD655: Mouse anti-DNP was applied to both probe slides with Liquid Coverslip™ and incubated for 32 minutes at 37° C.

10. The slide then underwent 3 rinses with reaction buffer before QD490:NDI C6 was incubated on the slide for 32 minutes with Liquid Coverslip™ at room temperature.

11. The slide was removed from the instrument and washed with reaction buffer twice. The slides were then dehydrated with graduated alcohol and xylene before manual application of a cover slip.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for visualizing a nucleus in a fixed tissue sample, comprising:
   pretreating a tissue sample with a protease to permeabilize the nucleus, thereby forming a pretreated tissue sample;
   incubating the pretreated tissue sample with a conjugate having a structure nanoparticle-linker-DNA-binding molecule, wherein the DNA binding molecule is selected from a minor groove binder, a major groove binder, a DNA intercalator, a DNA alkylating agent, or a combination thereof, under conditions sufficient to allow the conjugate to enter a nucleus within the pretreated tissue sample, wherein the conjugate binds to DNA in the nucleus; and
   visualizing the nanoparticle, and thereby visualizing the nucleus.

2. The method of claim 1, wherein the nanoparticle comprises a quantum dot, a metal nanoparticle, a metal oxide nanoparticle, or a transition metal complex nanoparticle.

3. The method of claim 1, wherein the nanoparticle comprises a quantum dot and visualizing the nanoparticle comprises visualizing photostable fluorescence of the quantum dot.

4. The method of claim 1, wherein the DNA-binding molecule is 4',6-diamidino-2-phenylindole (DAPI), a bisbenzimide dye, psoralen, or naphthalene diimide.

5. The method of claim 1, wherein the DNA-binding moiety is

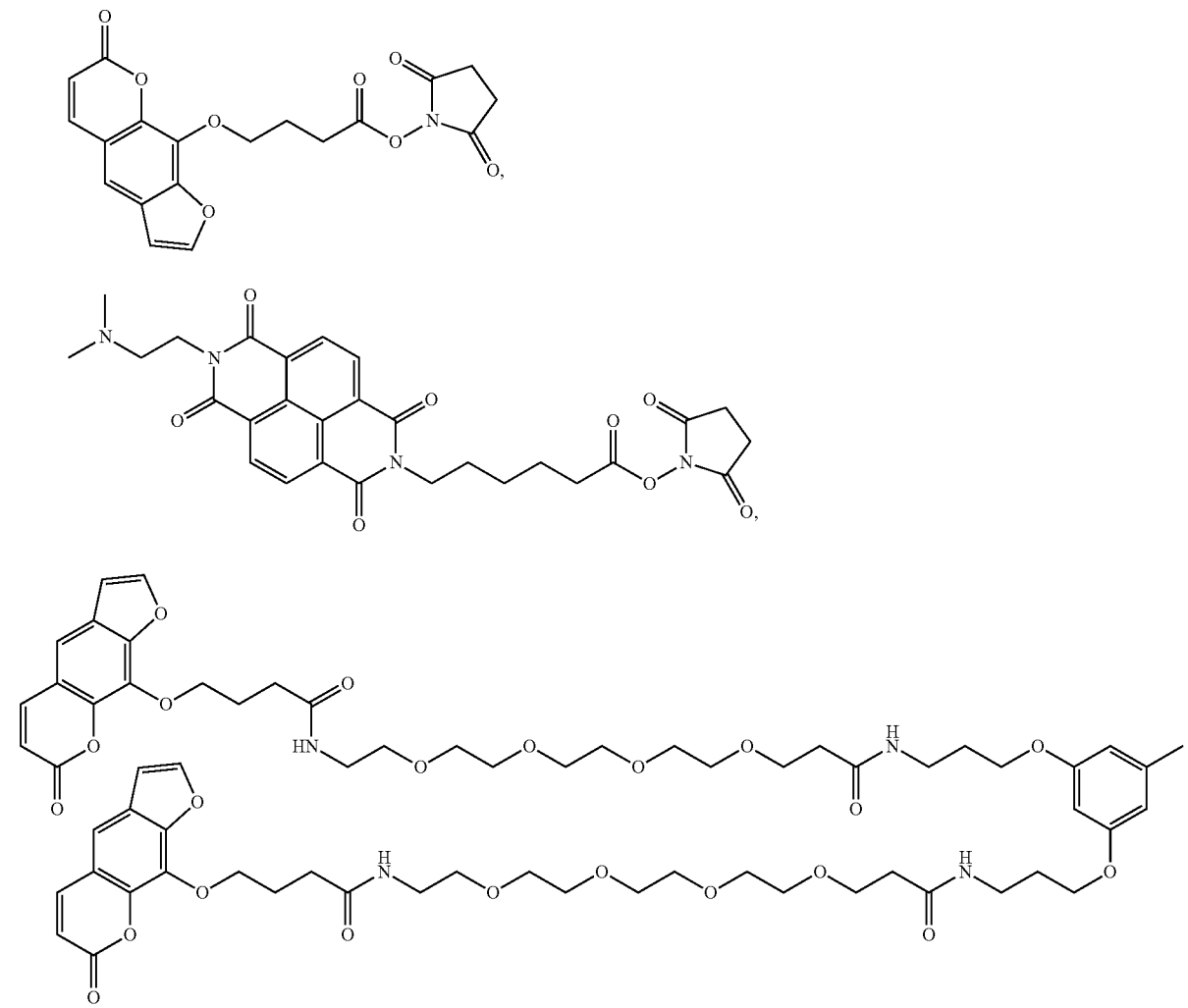

-continued

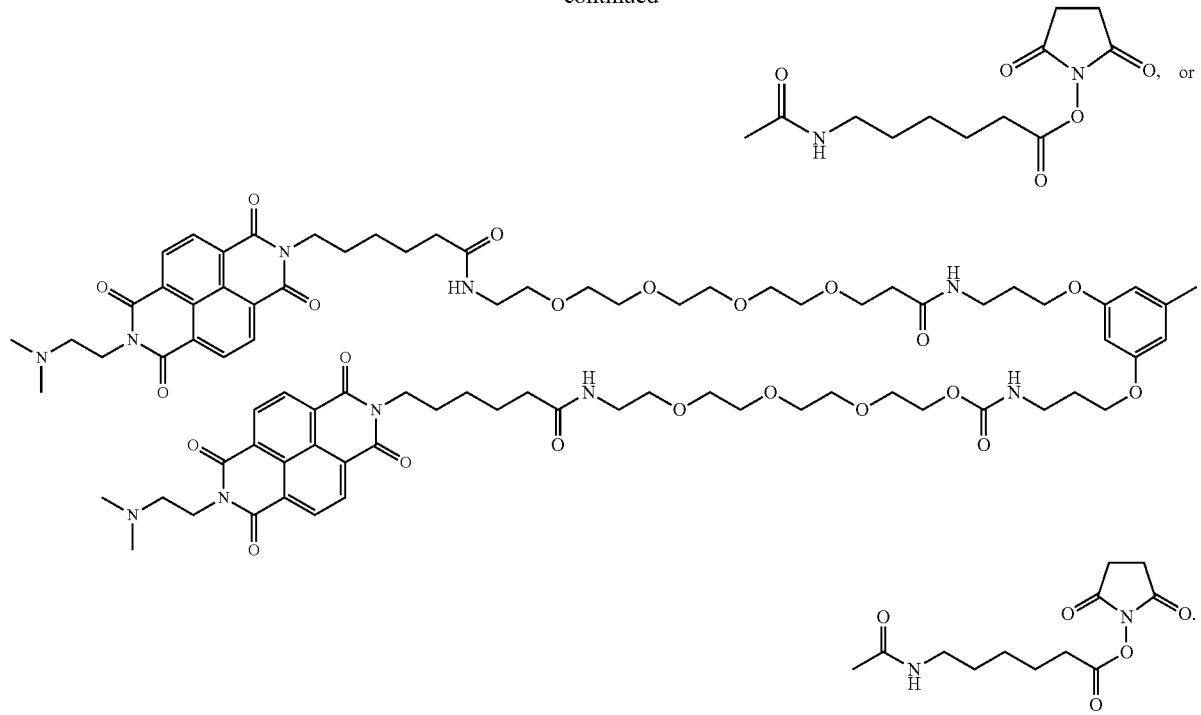

6. The method of claim 1, wherein the conjugate is incubated with the tissue sample at a concentration of at least 20 nM.

7. The method of claim 1, further comprising using computer image analysis techniques to quantitatively measure nuclear features.

8. The method of claim 7, wherein the nuclear features include chromosomal distribution, ploidy, shape, size, texture features, contextual features, or combinations thereof.

9. The method of claim 1, wherein the tissue sample is pretreated with the protease for 4-8 minutes and the tissue sample is fixed before pretreating with the protease.

10. The method of claim 1, further comprising:
providing a probe capable of hybridizing to a target within the tissue sample prior to incubating the pretreated tissue sample with the conjugate;
incubating the probe with the tissue sample under conditions sufficient to allow the probe to hybridize to the target within the tissue sample; and
detecting the probe.

11. The method of claim 10, wherein detecting the probe comprises visualizing a quantum dot associated with the probe.

12. The method of claim 11, wherein the nanoparticle of the conjugate comprises a quantum dot capable of emitting fluorescence at a different wavelength than the quantum dot associated with the probe.

13. The method of claim 1, further comprising performing a fluorescence in situ hybridization procedure on the tissue sample.

14. The method of claim 13, wherein the fluorescence in situ hybridization procedure comprises a HER2 assay, a TMPRSS2-ERG assay, a Chr17 assay, or a combination thereof.

15. A kit for visualizing a nucleus in a fixed tissue sample, comprising:
a protease enzyme composition comprising a protease enzyme and a protease buffer, wherein the protease buffer has a salt concentration and pH sufficient to allow the protease enzyme to exhibit proteolytic activity;
a conjugate having a structure nanoparticle-linker-DNA-binding molecule wherein the DNA-binding molecule is selected from a minor groove binder, a major groove binder, a DNA intercalator, a DNA alkylating agent, or a combination thereof; and
a reaction buffer, wherein the reaction buffer has a salt concentration and pH sufficient to enable the conjugate to enter a nucleus within a tissue sample pretreated with the protease enzyme composition.

16. The kit of claim 15, wherein the nanoparticle comprises a quantum dot, a metal nanoparticle, a metal oxide nanoparticle, or a transition metal complex nanoparticle.

* * * * *